US006951751B2

(12) United States Patent
Breinig et al.

(10) Patent No.: US 6,951,751 B2
(45) Date of Patent: Oct. 4, 2005

(54) DNA AND AMINO ACID SEQUENCES OF A TYROSINE-INDUCIBLE TYROSINE AMMONIA LYASE ENZYME FROM THE YEAST *TRICHOSPORON CUTANEUM*

(75) Inventors: Sabine Breinig, Philadelphia, PA (US); Wei Wei Qi, Broomall, PA (US); Fateme Sima Sariaslani, Wilmington, DE (US); Todd M. Vannelli, Ithaca, NY (US); Zhixiong Xue, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 12 days.

(21) Appl. No.: 10/439,479

(22) Filed: May 16, 2003

(65) Prior Publication Data

US 2004/0023357 A1 Feb. 5, 2004

Related U.S. Application Data

(60) Provisional application No. 60/383,232, filed on May 23, 2002.

(51) Int. Cl.[7] .............................. C12N 9/88; C12N 1/20; C12N 15/00; C12Q 1/68; C12P 7/42
(52) U.S. Cl. ................................. 435/232; 435/4; 435/6; 435/69.1; 435/136; 435/146; 435/183; 435/232; 435/252.3; 435/320.1; 435/410; 536/23.2
(58) Field of Search ................................. 453/69.1, 183, 453/232, 252.3, 320.1; 435/410; 536/23.2

(56) References Cited

U.S. PATENT DOCUMENTS

| 5,643,758 A | 7/1997 | Guan et al. |
| 6,368,837 B1 | 4/2002 | Gatenby et al. |
| 6,521,748 B2 | 2/2003 | Tang |

FOREIGN PATENT DOCUMENTS

| EP | 321488 B2 | 6/1996 |
| WO | WO 9307279 A1 | 4/1993 |
| WO | WO 9732023 A1 | 9/1997 |
| WO | WO 9811205 A2 | 3/1998 |

OTHER PUBLICATIONS

Broun et al. Science. Nov. 13, 1998;282(5392):1315–7.*
Fukuhara et al. Accession E01543. Sep. 29, 1997.*
Rosler et al., Maize Phenylalanine Ammonia–Lyase Has Tyrosine Ammonia–Lyase Activity, Plant Physiol., 1997, vol. 113:pp. 175–179.
Tang et al., Accession No. AAD26923, *Rhodotorula glutinis*, Apr. 9, 2002.

* cited by examiner

*Primary Examiner*—Manjunath N. Rao
*Assistant Examiner*—Christian L. Fronda

(57) ABSTRACT

A novel tyrosine-inducible tyrosine ammonia lyase enzyme was isolated from the yeast *Trichosporon cutaneum*. This enzyme has a higher activity for tyrosine than for phenylalanine and is useful for the production of para-hydroxycinnamic acid directly from tyrosine. The gene encoding this enzyme was sequenced using 3' and 5' RACE cloning of the TAL cDNA and the gene was expressed in the yeast *Saccharomyces cerevisiae* and in the bacterium *Escherichia coli*.

15 Claims, 3 Drawing Sheets

SEQUENCE LISTING

<160> NUMBER OF SEQ ID NOS: 34

<210> SEQ ID NO 1
<211> LENGTH: 26
<212> TYPE: PRT
<213> ORGANISM: T. cutaneum

<400> SEQUENCE: 1

Met Phe Ile Glu Thr Asn Val Ala Lys Pro Ala Ser Thr Lys Ala Met
1               5                   10                  15

Asn Ala Gly Ser Ala Lys Ala Ala Pro Val
            20                  25

<210> SEQ ID NO 2
<211> LENGTH: 20
<212> TYPE: PRT
<213> ORGANISM: T. cutaneum

<400> SEQUENCE: 2

Phe Gly Gly Ser Ala Asp Thr Arg Thr Ser Asp Thr Glu Ala Leu Gln
1               5                   10                  15

Ile Ala Leu Leu
            20

<210> SEQ ID NO 3
<211> LENGTH: 44
<212> TYPE: DNA
<213> ORGANISM: Artificial Sequence
<220> FEATURE:
<223> OTHER INFORMATION: Primer

<400> SEQUENCE: 3
gagaccaacg tcgccaagcc cgcctcgacc aaggccatga acgc                           44

<210> SEQ ID NO 4
<211> LENGTH: 44
<212> TYPE: DNA
<213> ORGANISM: Artificial Sequence
<220> FEATURE:
<223> OTHER INFORMATION: Primer

<400> SEQUENCE: 4

```
gagaccaacg tcgccaagcc cgccagcacc aaggccatga acgc            44
```

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5

```
gccgacaccc gcacctcgga cacbgaggc                              29
```

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6

```
ggcaatctgg agggcctcvg tgtc                                   24
```

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7

```
gtcctggtcg gcgaggagct cgggctcctc gtg                         33
```

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8

```
gcctcgagct gggggccrat ccactg                                 26
```

<210> SEQ ID NO 9
<211> LENGTH: 1092
<212> TYPE: DNA
<213> ORGANISM: T. cutaneum

<400> SEQUENCE: 9

```
gagaccaatg tcgccaagcc cgcttccacc aaggcgatga acgccggttc ggccaaggcc    60
gctcctgtgt gagtacccac cactaactgg ggagtcaccg ctgacatgca gtgagccgtt   120
cgctacctat gcccactccc aggctaccaa gaccgtcagc atcgacggcc acaccatgaa   180
ggtcggtgac gtcgtcgccg tcgcccgcca cggcgccaag gtcgagctcg cggcctcggt   240
cgccggcccc gtccgggcct cggtcgactt caaggagtcc aagaagcaca cgtcgatcta   300
cggcgtcacc accggctttg gcggctcggc cgacacgcgc accagcgaca ccgaggcgct   360
ccagatctcg ctcctcgagc accagctctg cggcttcctc cccaccgacg ccacctacga   420
gggcatgctc ctcgccgcga tgccgatccc atcgtccgc ggcgccatgg ccgtccgcgt   480
caacagctgc gtccgcggcc actcgggcgt ccgcctcgag gtcctccagt cgtttgccga   540
ctttatcaac agaggcctcg tcccctgcgt gccctccgc ggcaccatct cggcctcggg   600
cgacctctcg ccctctcgt acattgccgg tgcgatctgc ggccaccccg acgtcaaggt   660
```

```
gttcgacacc gcggcgtcgc ccccacggt tctcacctcc cccgaggcga tcgccaagta    720
cggcctcaag accgtcaagc tcgcctccaa ggagggcctc ggcctcgtca acggcacggc    780
cgtctcggcg gccgcgggcg cgctcgcgct ctacgacgcc gagtgcctcg ccatcatgag    840
ccagaccaac actgtgctca cggtcgaggc gctcgacggc cacgtcggct cgtttgcccc    900
cttcatccag gagatccgcc ctcacgccgg ccagatcgag gccgctagaa acattagaca    960
catgctcggt ggctccaagc tcgccgtgca cgaggagtcc gagctcctcg ccgaccagga   1020
cgccggcatc ctccgccagg accgctacgc gctccgcacc tcggcgcagt ggatcggccc   1080
gcagctcgag gc                                                        1092
```

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggaggggcac gcaggggacg                                                  20

<210> SEQ ID NO 11
<211> LENGTH: 22
<212> TYPE: DNA
<213> ORGANISM: artificial sequence
<220> FEATURE:
<223> OTHER INFORMATION: primer

<400> SEQUENCE: 11
ggaggggcac gcaggggacg ag                                               22

<210> SEQ ID NO 12
<211> LENGTH: 19
<212> TYPE: DNA
<213> ORGANISM: artificial sequence
<220> FEATURE:
<223> OTHER INFORMATION: primer

<400> SEQUENCE: 12
cggcaaacga ctggaggac                                                   19

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
taggtggcgt cggtggggag gaag                                             24

<210> SEQ ID NO 14
<211> LENGTH: 21
<212> TYPE: DNA
<213> ORGANISM: artificial sequence
<220> FEATURE:
<223> OTHER INFORMATION: primer

<400> SEQUENCE: 14
ggtggggagg aagccgcaga g                                                21

<210> SEQ ID NO 15

```
<211> LENGTH: 21
<212> TYPE: DNA
<213> ORGANISM: artificial sequence
<220> FEATURE:
<223> OTHER INFORMATION: Primer

<400> SEQUENCE: 15
atggccgtcc gcgtcaacag c                                              21

<210> SEQ ID NO 16
<211> LENGTH: 23
<212> TYPE: DNA
<213> ORGANISM: artificial sequence
<220> FEATURE:
<223> OTHER INFORMATION: Primer

<400> SEQUENCE: 16
atctcggcct cgggcgacct ctc                                            23

<210> SEQ ID NO 17
<211> LENGTH: 21
<212> TYPE: DNA
<213> ORGANISM: artificial sequence
<220> FEATURE:
<223> OTHER INFORMATION: Primer

<400> SEQUENCE: 17
accccgacgt caaggcgttc g                                              21

<210> SEQ ID NO 18
<211> LENGTH: 26
<212> TYPE: DNA
<213> ORGANISM: artificial sequence
<220> FEATURE:
<223> OTHER INFORMATION: Primer

<400> SEQUENCE: 18
gcgatcgcca agtacggcct caagac                                         26

<210> SEQ ID NO 19
<211> LENGTH: 25
<212> TYPE: DNA
<213> ORGANISM: artificial sequence
<220> FEATURE:
<223> OTHER INFORMATION: Primer

<400> SEQUENCE: 19
cctccaagga gggcctcggc ctcgt                                          25

<210> SEQ ID NO 20
<211> LENGTH: 28
<212> TYPE: DNA
<213> ORGANISM: artificial sequence
<220> FEATURE:
<223> OTHER INFORMATION: Primer

<400> SEQUENCE: 20
ctcgccatca tgagccagac caacactg                                       28

<210> SEQ ID NO 21
<211> LENGTH: 30
<212> TYPE: DNA
<213> ORGANISM: artificial sequence
<220> FEATURE:
<223> OTHER INFORMATION: primer

<400> SEQUENCE: 21
```

```
ggccacgcgt cgactagtac gggggggggg                                      30

<210> SEQ ID NO 22
<211> LENGTH: 32
<212> TYPE: DNA
<213> ORGANISM: artificial sequence
<220> FEATURE:
<223> OTHER INFORMATION: primer

<400> SEQUENCE: 22
cuacuacuac uaggccacgc gtcgactagt ac                                   32

<210> SEQ ID NO 23
<211> LENGTH: 710
<212> TYPE: DNA
<213> ORGANISM: T.cutaneum

<400> SEQUENCE: 23 gggggggtgga atgcatgctc cggcgacagc ccggcatacc acactgtaac acactcgtct    60
cccccctccc accctctctt atcgcgtcac atggctaact ctctgactgc tcgcacctaa    120
cacgaacacg gcgccgagcg aggcgatgaa cgctatataa caatccgtgg tgttgccacc    180
tcctccccac cgatcacact cagctcagct cgctcctcgc cagcccctct cgctctaact    240
cgctctacgc tatcgcggta ccgcacccca tacaacaaac ccctcccgag tggcaatgtt    300
tattgagacc aatgtcgcca agcccgcttc caccaaggcg atgaacgccg gttcggccaa    360
ggccgctcct gtgtgagtac ccaccactaa ctggggagtc accgctgaca tgcagtgagc    420
cgttcgctac ctatgcccac tcccaggcta ccaagaccgt cagcatcgac ggccacacca    480
tgaaggtcgg tgacgtcgtc gccgtcgccc gccacgcgc caaggtcgag ctcgcggcct    540
cggtcgccgg ccccgtccgg gcctcggtcg acttcaagga gtccaagaag cacacgtcga    600
tctacggcgt caccaccggc tttggcggct cggccgacac gcgcaccagc gacaccgagg    660
cgctccagat ctcgctcctc gagcaccagc tctgcggctt cctccccacc                710

<210> SEQ ID NO 24
<211> LENGTH: 2465
<212> TYPE: DNA
<213> ORGANISM: T. cutaneum
<220> FEATURE:
<221> NAME/KEY: misc_feature
<222> LOCATION: (1607)..(1607)
<223> OTHER INFORMATION: n=a,c,t,g

<400> SEQUENCE: 24
tggaatgcat gctccggcga cagcccggca taccacactg taacacactc gtctcccccc    60
tcccaccctc tcttatcgcg tcacatggct aactctctga ctgctcgcac ctaacacgaa    120
cacggcgccg agcgaggcga tgaacgctat ataacaatcc gtggtgttgc cacctcctcc    180
ccaccgatca cactcagctc agctcgctcc tcgccagccc ctctcgctct aactcgctct    240
acgctatcgc ggtaccgcac cccatacaac aaacccctcc cgagtggcaa tgttttattga   300 gaccaatgtc gccaagcccg cttccaccaa ggcgatgaac gccggttcgg ccaaggccgc    360
tcctgtgtga gtaccccacca ctaactgggg agtcaccgct gacatgcagt gagccgttcg    420
ctacctatgc ccactcccag gctaccaaga ccgtcagcat cgacggccac accatgaagg    480
tcggtgacgt cgtcgccgtc gccgccacg gcgccaaggt cgagctcgcg gcctcggtcg    540 ccggcccccgt ccgggcctcg gtcgacttca aggagtccaa gaagcacacg tcgatctacg    600
```

```
gcgtcaccac cggctttggc ggctcggccg acacgcgcac cagcgacacc gaggcgctcc     660
agatctcgct cctcgagcac cagctctgcg gcttcctccc caccgacgcc acctacgagg     720
gcatgctcct cgccgcgatg ccgatcccca tcgtccgcgg cgccatggcc gtccgcgtca     780
acagctgcgt ccgcggccac tcgggcgtcc gcctcgaggt cctccagtcg tttgccgact     840
ttatcaacag aggcctcgtc ccctgcgtgc cctccgcgg caccatctcg gcctcgggcg      900
acctctcgcc cctctcgtac attgccggtg cgatctgcgg ccaccccgac gtcaaggtgt     960
tcgacaccgc ggcgtcgccc ccacggttc tcacctcccc cgaggcgatc gccaagtacg     1020
gcctcaagac cgtcaagctc gcctccaagg agggcctcgg cctcgtcaac ggcacggccg    1080
tctcggcggc cgcgggcgcg ctcgcgctct acgacgccga gtgcctcgcc atcatgagcc    1140
agaccaacac tgtgctcacg gtcgaggcgc tcgacggcca cgtcggctcg tttgcccct     1200
tcatccagga gatccgccct cacgccggcc agatcgaggc cgctagaaac attagacaca    1260
tgctcggtgg ctccaagctc gccgtgcacg aggagtccga gctcctcgcc gaccaggacg    1320
ccggcatcct ccgccaggac cgctacgcgc tccgcacctc ggcgcagtgg atcggcccgc    1380
agctcgaggc gctcggcctc gcccgccagc agatcgagac cgagctcaac tcgaccaccg    1440
acaaccgct catcgatgtc gagggcggca tgttccacca cggcggcaac ttccaggcca     1500
tggccgtcac ctcggccatg gactcggccc gcatcgtcct ccagaacctc ggcaagctca    1560
gctttgccca ggtcaccgag ctcatcaact gcgagatgaa ccacggnctc ccctccaacc    1620
tcgccggctc cgagcctagc accaactacc actgcaaggg tctcgacatc cactgcggcg    1680
cctactgcgc cgagctcggc ttcctcgcca accccatgag caaccacgtc cagagcaccg    1740
agatgcacaa ccagagcgtg aactcgatgg cgttcgcgtc cgcccgcagg acgatggagg    1800
ccaacgaggt cctctcgctc ctcctcggct cgcagatgta ctgcgcgacc caggccctcg    1860
acctccgcgt catggaggtc aagttcaaga tggccatcgt caagctcctc aacgagaccc    1920
tcaccaagca ctttgcggcc ttcctcacgc ccgagcagct cgccaagctc aacacccacg    1980
ccgccatcac gctgtacaag cgcctcaacc agacgcccag ctgggactcg ccccgcgct     2040
tcgaggacgc cgccaagcac ctcgtcggcg tcatcatgga cgccctcatg gtcaacgacg    2100
acatcaccga cctcaccaac ctccccaagt ggaagaagga gttcgccaag gaggccggca    2160
acctctaccg ctcgatcctc gtcgcgacca ccgccgacgg ccgcaacgac ctcgagcccg    2220
ccgagtacct cggccagacg cgcgccgtct acgaggccgt ccgctccgag ctcggcgtca    2280
aggtccgccg cggcgacgtc gccgagggca agagcggcaa gagcatcggc tcgagcgtcg    2340
ccaagatcgt cgaggcgatg cgcgacggcc gcctcatggg cgctgttggc aagatgttct    2400
aagccaccag acatttctct atagggtagc aactgtttca gtagcacatg catcattgta    2460
ctatt                                                                 2465
```

<210> SEQ ID NO 25
<211> LENGTH: 689
<212> TYPE: PRT
<213> ORGANISM: T. cutaneum

<400> SEQUENCE: 25

Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
            20                  25                  30

Ala His Ser Gln Ala Thr Lys Thr Val Ser Ile Asp Gly His Thr Met

```
            35                  40                  45
Lys Val Gly Asp Val Val Ala Val Ala Arg His Gly Ala Lys Val Glu
 50                  55                  60

Leu Ala Ala Ser Val Ala Gly Pro Val Arg Ala Ser Val Asp Phe Lys
 65                  70                  75                  80

Glu Ser Lys Lys His Thr Ser Ile Tyr Gly Val Thr Thr Gly Phe Gly
                 85                  90                  95

Gly Ser Ala Asp Thr Arg Thr Ser Asp Thr Glu Ala Leu Gln Ile Ser
                100                 105                 110

Leu Leu Glu His Gln Leu Cys Gly Phe Leu Pro Thr Asp Ala Thr Tyr
            115                 120                 125

Glu Gly Met Leu Leu Ala Ala Met Pro Ile Pro Ile Val Arg Gly Ala
            130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Arg Gly Leu Val
                165                 170                 175

Pro Cys Val Pro Leu Arg Gly Thr Ile Ser Ala Ser Gly Asp Leu Ser
                180                 185                 190

Pro Leu Ser Tyr Ile Ala Gly Ala Ile Cys Gly His Pro Asp Val Lys
            195                 200                 205

Val Phe Asp Thr Ala Ala Ser Pro Pro Thr Val Leu Thr Ser Pro Glu
210                 215                 220

Ala Ile Ala Lys Tyr Gly Leu Lys Thr Val Lys Leu Ala Ser Lys Glu
225                 230                 235                 240

Gly Leu Gly Leu Val Asn Gly Thr Ala Val Ser Ala Ala Gly Ala
                245                 250                 255

Leu Ala Leu Tyr Asp Ala Glu Cys Leu Ala Ile Met Ser Gln Thr Asn
                260                 265                 270

Thr Val Leu Thr Val Glu Ala Leu Asp Gly His Val Gly Ser Phe Ala
            275                 280                 285

Pro Phe Ile Gln Glu Ile Arg Pro His Ala Gly Gln Ile Glu Ala Ala
            290                 295                 300

Arg Asn Ile Arg His Met Leu Gly Gly Ser Lys Leu Ala Val His Glu
305                 310                 315                 320

Glu Ser Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Ala Leu Gly Leu Ala Arg Gln Gln Ile Glu Thr Glu Leu Asn Ser Thr
            355                 360                 365

Thr Asp Asn Pro Leu Ile Asp Val Glu Gly Gly Met Phe His His Gly
370                 375                 380

Gly Asn Phe Gln Ala Met Ala Val Thr Ser Ala Met Asp Ser Ala Arg
385                 390                 395                 400

Ile Val Leu Gln Asn Leu Gly Lys Leu Ser Phe Ala Gln Val Thr Glu
                405                 410                 415

Leu Ile Asn Cys Glu Met Asn His Gly Leu Pro Ser Asn Leu Ala Gly
                420                 425                 430

Ser Glu Pro Ser Thr Asn Tyr His Cys Lys Gly Leu Asp Ile His Cys
            435                 440                 445

Gly Ala Tyr Cys Ala Glu Leu Gly Phe Leu Ala Asn Pro Met Ser Asn
450                 455                 460
```

```
His Val Gln Ser Thr Glu Met His Asn Gln Ser Val Asn Ser Met Ala
465                 470                 475                 480

Phe Ala Ser Ala Arg Arg Thr Met Glu Ala Asn Glu Val Leu Ser Leu
                485                 490                 495

Leu Leu Gly Ser Gln Met Tyr Cys Ala Thr Gln Ala Leu Asp Leu Arg
            500                 505                 510

Val Met Glu Val Lys Phe Lys Met Ala Ile Val Lys Leu Leu Asn Glu
        515                 520                 525

Thr Leu Thr Lys His Phe Ala Ala Phe Leu Thr Pro Glu Gln Leu Ala
    530                 535                 540

Lys Leu Asn Thr His Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
                565                 570                 575

Leu Val Gly Val Ile Met Asp Ala Leu Met Val Asn Asp Ile Thr
            580                 585                 590

Asp Leu Thr Asn Leu Pro Lys Trp Lys Lys Glu Phe Ala Lys Glu Ala
        595                 600                 605

Gly Asn Leu Tyr Arg Ser Ile Leu Val Ala Thr Thr Ala Asp Gly Arg
    610                 615                 620

Asn Asp Leu Glu Pro Ala Glu Tyr Leu Gly Gln Thr Arg Ala Val Tyr
625                 630                 635                 640

Glu Ala Val Arg Ser Glu Leu Gly Val Lys Val Arg Arg Gly Asp Val
                645                 650                 655

Ala Glu Gly Lys Ser Gly Lys Ser Ile Gly Ser Ser Val Ala Lys Ile
            660                 665                 670

Val Glu Ala Met Arg Asp Gly Arg Leu Met Gly Ala Val Gly Lys Met
        675                 680                 685

Phe

<210> SEQ ID NO 26
<211> LENGTH: 22
<212> TYPE: DNA
<213> ORGANISM: artificial sequence
<220> FEATURE:
<223> OTHER INFORMATION: Primer

<400> SEQUENCE: 26
atgtttattg agaccaatgt cg                                              22

<210> SEQ ID NO 27
<211> LENGTH: 41
<212> TYPE: DNA
<213> ORGANISM: artificial sequence
<220> FEATURE:
<223> OTHER INFORMATION: Primer

<400> SEQUENCE: 27
cataggtagc gaacggctcc acaggagcgg ccttggccga a                         41

<210> SEQ ID NO 28
<211> LENGTH: 41
<212> TYPE: DNA
<213> ORGANISM: artificial sequence
<220> FEATURE:
<223> OTHER INFORMATION: Primer

<400> SEQUENCE: 28
```
ttcggccaag gccgctcctg tgagccgtt cgctacctat g       41

<210> SEQ ID NO 29
<211> LENGTH: 32
<212> TYPE: DNA
<213> ORGANISM: artificial sequence
<220> FEATURE:
<223> OTHER INFORMATION: Primer

<400> SEQUENCE: 29
gatcgaattc tagagaaatg tctggtggct ta       32

<210> SEQ ID NO 30
<211> LENGTH: 33
<212> TYPE: DNA
<213> ORGANISM: artificial sequence
<220> FEATURE:
<223> OTHER INFORMATION: Primer

<400> SEQUENCE: 30
gatcgaattc atgtttattg agaccaatgt cgc       33

<210> SEQ ID NO 31
<211> LENGTH: 31
<212> TYPE: DNA
<213> ORGANISM: artificial sequence
<220> FEATURE:
<223> OTHER INFORMATION: Primer

<400> SEQUENCE: 31
gatctctaga ttagaacatc ttgccaacag c       31

<210> SEQ ID NO 32
<211> LENGTH: 35
<212> TYPE: DNA
<213> ORGANISM: artificial sequence
<220> FEATURE:
<223> OTHER INFORMATION: primer

<400> SEQUENCE: 32
caggagatcc atatgtttat tgagaccaat gtcgc       35

<210> SEQ ID NO 33
<211> LENGTH: 30
<212> TYPE: DNA
<213> ORGANISM: artificial sequence
<220> FEATURE:
<223> OTHER INFORMATION: primer

<400> SEQUENCE: 33
gatcaagctt ttagaacatc ttgccacagc       30

<210> SEQ ID NO 34
<211> LENGTH: 619
<212> TYPE: DNA
<213> ORGANISM: Oryza sativa

<400> SEQUENCE: 34
catatggcgg agacggcggc ggtcgggacg gcggaggagc cgctgctggt gagcgcgatc       60
aaggggagga aggtcgagag accgccggtc tggctcatga ggcaggccgg gaggtacatg      120
aagagctatc aattgctctg cgagcgacat ccttcattc cgtgaaagat cagaaaatgt      180
tgaccttgtt gttgctacat taaataccaa gctgacaacg gagcacaagc tgtccaaatt      240
tttgactcat gggctacaga actcagccca gttgattttg aggagtttag cttgccttat      300

```
ctgaagcaga ttgtggatag tgtcaaagaa acacatcctg aattgcctct gatactatat      360
gcaagtggat ctggtggact gctggagagg cttccactga caggtgttga tgttgttagc      420
ttggactgga cggttgatat ggctgagggg aggaaaagat tgggaatagt gggcatgtat      480
tgaaccttgg tcatggcatt aaggtaggca ctcctgagga aaatgttgcc catttctttg      540
aggttgcaaa agggatcaga tactgaaata cctaggctat tcgatgcatt cctttctccc      600
tagttcgccc tatggatcc                                                   619
```

DNA AND AMINO ACID SEQUENCES OF A TYROSINE-INDUCIBLE TYROSINE AMMONIA LYASE ENZYME FROM THE YEAST *TRICHOSPORON CUTANEUM*

This application claims the benefit of U.S. Provisional Application No. 60/383,232, filed May 23, 2002.

FIELD OF THE INVENTION

The invention relates to the field of molecular biology and microbiology. More specifically, the invention relates to the nucleotide and amino acid sequences of a novel tyrosine-inducible tyrosine ammonia lyase enzyme from the yeast *Trichosporon cutaneum* to be used for production of para-hydroxycinnamic acid (PHCA).

BACKGROUND OF THE INVENTION

Para-hydroxycinnamic acid (PHCA) is a high-value, aromatic chemical compound that may be used as a monomer for the production of Liquid Crystal Polymers (LCP). LCPs are polymers that exhibit an intermediate or mesophase between the glass-transition temperature and the transition temperature to the isotropic liquid or have at least one mesophase for certain ranges of concentration and temperature. The molecules in these mesophases behave like liquids and flow, but also exhibit the anisotropic properties of crystals. LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging.

Due to its importance as a high value, aromatic chemical compound, chemical synthesis of PHCA is known. However, chemical synthesis is expensive due to the high energy needed for synthesis and the extensive product purification required. Biological production of PHCA offers a low cost, simplified solution to the problem.

The production of PHCA by plants using the enzymes phenylalanine ammonia lyase (PAL) (EC 4.3.1.5) and a P450 enzyme is well known. Phenylalanine ammonia-lyase is widely distributed in plants (Koukol et al., *J. Biol. Chem.* 236:2692–2698 (1961)), fungi (Bandoni et al., *Phytochemistry* 7:205–207 (1968)), yeast (Ogata et al., *Agric. Biol. Chem.* 31:200–206 (1967)), and *Streptomyces* (Emes et al., *Can. J. Microbiology* 48:613–622 (1970)), but it has not been found in *Escherichia coli* or mammalian cells (Hanson and Havir In *The Enzymes*, 3$^{rd}$ ed.; Boyer, P., Ed.; Academic: New York, 1967; pp 75–167). PAL is the first enzyme of phenylpropanoid metabolism and catalyzes the removal of the (pro-3S)-hydrogen and —NH$_3^+$ from L-phenylalanine to form trans-cinnamic acid. In the presence of a P450 enzyme system, trans-cinnamic acid can be converted to para-hydroxycinnamic acid (PHCA) which serves as the common intermediate in plants for production of various secondary metabolites such as lignin and isoflavonoids. In microbes however, cinnamic acid and not PHCA acts as the precursor for secondary metabolite formation. No cinnamate hydroxylase enzyme has so far been characterized from microbial sources. The PAL enzyme in plants is thought to be a regulatory enzyme in the biosynthesis of lignin, isoflavonoids and other phenylpropanoids (Hahlbrock et al., *Annu. Rev. Plant Phys. Plant Mol. Biol.* 40:347–369 (1989)). However, in the red yeast, *Rhodotorula glutinis* (*Rhodosporidium toruloides*), this lyase degrades phenylalanine as a catabolic function and the cinnamate formed by the action of this enzyme is converted to benzoate and other cellular materials.

Genes encoding PAL are known in the art and several have been sequenced from both plant and microbial sources (see for example EP 321488 [*Rhodosporidium toruloides*]; WO 9811205 [*Eucalyptus grandis* and *Pinus radiata*]; WO 9732023 [*Petunia*]; JP 05153978 [*Pisum sativum*]; WO 9307279 [potato, rice]; and for example GenBank AJ010143 and X75967). The PAL genes from various sources have been over-expressed as active PAL enzymes in yeast, *Escherichia coli* and insect cell cultures (Faulkner et al., *Gene* 143:13–20 (1994); Langer et al., *Biochemistry* 36:10867–10871 (1997); McKegney et al., *Phytochemistry* 41:1259–1263 (1996)).

Some PAL genes, in addition to their ability to convert phenylalanine to cinnamate, can accept tyrosine as substrate. In such reactions the enzyme activity is designated tyrosine ammonia lyase (TAL). Conversion of tyrosine by TAL results in the direct formation of PHCA from tyrosine without the intermediacy of cinnamate. However, there has been only one, very recent report of a gene which encodes an enzyme having significantly higher TAL catalytic activity than PAL activity (Kyndt et al., *FEBS Letters* 512:240–244 (2002)). This gene was isolated from the bacterium *Rhodobacter capsulatus* and encoded an enzyme that had a TAL catalytic efficiency that was approximately 150 times higher than that for PAL. This TAL protein was reported to have a higher homology to the PAL proteins of plants (e.g., 32% identity with the PAL sequence of *Pinus taeda*), than to the PAL sequences of yeasts. All other natural PAL/TAL enzymes prefer to use phenylalanine rather than tyrosine as their substrate. The wild-type PAL/TAL enzyme from the yeast *Rhodosporidium* exhibits a reduced preference for phenylalanine as compared to tyrosine, having a ratio of TAL catalytic activity to PAL catalytic activity of only 0.58 (reported in Hanson and Havir, In *The Biochemistry of Plants*; Academic: New York, 1981; Vol. 7, pp 577–625). For comparison, the PAL/TAL enzymes studied in other organisms typically possess PAL/TAL ratios of 15 or greater.

U.S. Pat. No. 6,368,837 discloses several methods for the biological production of PHCA. These include: the incorporation of the wild type PAL from the yeast *Rhodotorula glutinis* into *E. coli* and utilizing the ability of the wild type PAL to convert tyrosine to PHCA; the incorporation of the wild type PAL from the yeast *Rhodotorula glutinis* plus the plant cytochrome P-450 and the P-450 reductase into *E. coli* to convert phenylalanine to cinnamic acid and then to PHCA; and the development of a mutant PAL/TAL gene that encoded an enzyme with enhanced TAL activity. This mutant gene was isolated by mutagenesis of the wild type *Rhodosporidium toruloides* PAL and encoded an enzyme with a TAL/PAL ratio of 1.7. This gene was used to produce PCHA by direct conversion of tyrosine. The development of several other mutant PAL/TAL genes that encode enzymes with enhanced TAL activity is disclosed in U.S. Pat. No. 6,521,748. TAL/PAL ratios up to 7.2 were reported from these mutant genes. However, other PAL/TAL enzymes with higher TAL activity are required for the economical production of PCHA.

The problem to be solved therefore is to obtain a naturally occurring enzyme with higher TAL than PAL activity to be used for the direct conversion of tyrosine to PHCA and to serve as a tool for future enzyme engineering to produce more efficient TAL enzymes. Applicants have solved the stated problem by isolating an enzyme from *Trichosporon cutanem* that has a higher TAL catalytic activity than PAL activity. Furthermore, the gene for this enzyme is induced by the presence of tyrosine rather than phenylalanine.

SUMMARY OF THE INVENTION

The invention provides an isolated nucleic acid molecule encoding a tyrosine ammonia lyase enzyme, selected from the group consisting of:

a) an isolated nucleic acid molecule encoding the amino acid sequence as set forth in SEQ ID NO:25;

b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid molecule that is complementary to (a) or (b).

Additionally the invention provides polypeptides encoded by the nucleic acids of the invention as well as genetic chimera and transformed host cells containing the same.

In another embodiment the invention provides a method of obtaining a nucleic acid molecule encoding a tyrosine ammonia lyase enzyme comprising:

a) probing a genomic library with the nucleic acid molecule of the invention b) identifying a DNA clone that hybridizes with the nucleic acid molecule of the invention; and c) sequencing the genomic fragment that comprises the clone identified in step (b), wherein the sequenced genomic fragment encodes a tyrosine ammonia lyase enzyme.

Similarly the invention provides a method of obtaining a nucleic acid molecule encoding a tyrosine ammonia lyase enzyme comprising:

a) synthesizing at least one oligonucleotide primer corresponding to a portion of the sequence as set forth in SEQ ID NO:24; and b) amplifying an insert present in a cloning vector using the oligonucleotide primer of step (a);

wherein the amplified insert encodes a portion of an amino acid sequence encoding a tyrosine ammonia lyase enzyme.

In a preferred embodiment the invention provides a method for the production of PHCA comprising:

(a) contacting a recombinant host cell with a fermentable carbon substrate, said recombinant cell comprising the isolated nucleic acid molecule of the invention operably linked to suitable regulatory sequences;

(b) growing said recombinant cell for a time sufficient to produce PHCA; and (c) optionally recovering said PHCA.

BRIEF DESCRIPTION OF THE FIGURES AND SEQUENCE DESCRIPTIONS

The invention can be more fully understood from the following detailed description, figures and the accompanying sequence descriptions, which form a part of this application.

Figure 1:
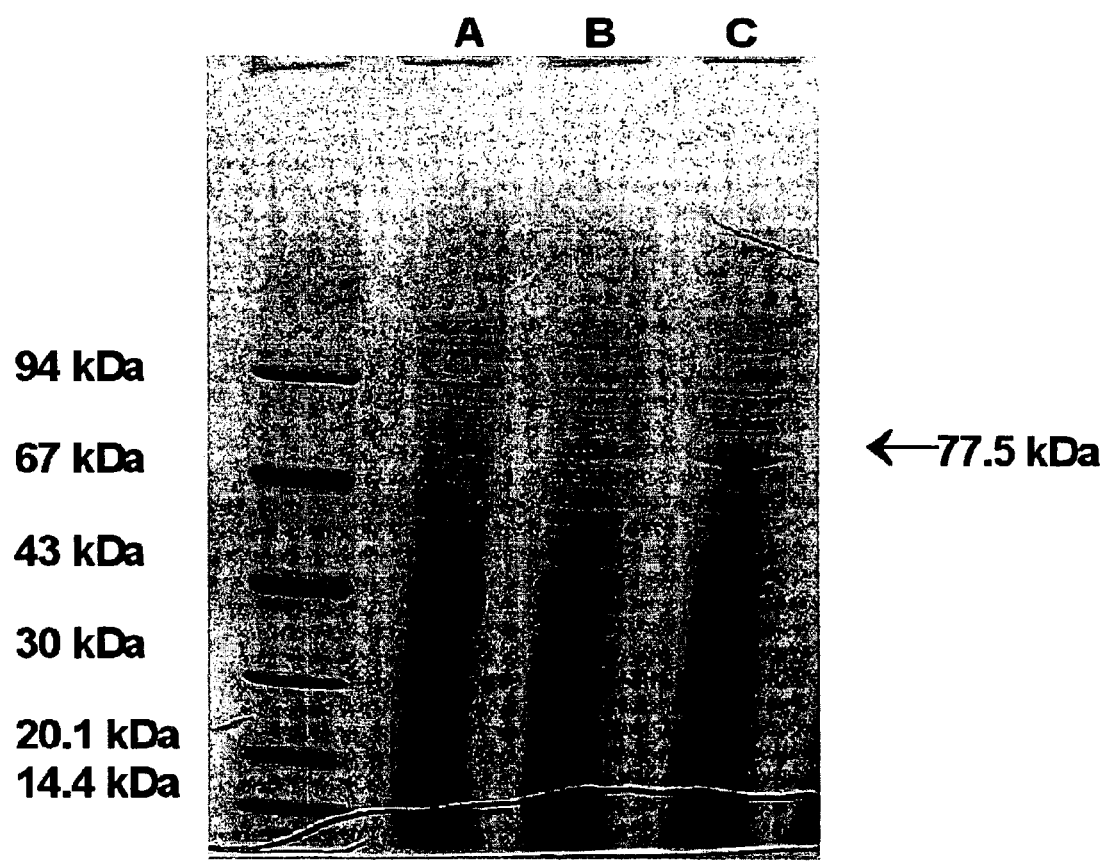
FIG. 1 is a gel image of the polyacrylamide gel electrophoresis of cell-free extracts of *T. cutaneum*.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the N-terminal amino acid sequence of the TAL enzyme from *T. cutaneum*.

SEQ ID NO:2 is an internal amino acid sequence of the TAL enzyme from *T. cutaneum*.

SEQ ID NOs:3–8 are oligonucleotide primers used for cloning of the *T. cutaneum* tal.

SEQ ID NO:9 is a consensus nucleotide sequence of TAL genomic DNA.

SEQ ID NOs:10–22 are oligonucleotide primers used for cloning of the *T. cutaneum* tal.

SEQ ID NO:23 is a second consensus nucleotide sequence of TAL genomic DNA.

SEQ ID NO:24 is the nucleotide sequence of the TAL cDNA from *T. cutaneum*.

SEQ ID NO:25 is the deduced amino acid sequence of the TAL from *T. cutaneum* encoded by the nucleotide sequence of SEQ ID NO:24.

SEQ ID NOs:26–33 are oligonucleotide primers used for cloning of the *T. cutaneum* tal.

SEQ ID NO:34 is a DNA fragment from *Oryza sativa* that was used as part of the plasmid which was used to express tal in *E. coli*.

DETAILED DESCRIPTION OF THE INVENTION

The present invention describes a new DNA sequence that encodes a tryosine-inducible tyrosine ammonia lyase enzyme from the yeast *Trichosporan cutaneum*. This enzyme is only the second naturally occurring PAL/TAL enzyme reported with a higher specific activity when tyrosine is used as the substrate as opposed to phenylalanine. This TAL enzyme can be used for the production of PHCA directly from tyrosine.

Definitions

The following abbreviations and definitions will be used for the interpretation of the specification and the claims.

"Phenylalanine ammonia-lyase" is abbreviated PAL.

"Tyrosine ammonia-lyase" is abbreviated TAL.

"Para-hydroxycinnamic acid" is abbreviated PHCA.

"Cinnamate 4-hydroxylase" is abbreviated C4H.

As used herein the terms "cinnamic acid" and "cinnamate" are used interchangeably and are abbreviated CA.

The term "TAL activity" refers to the ability of a protein to catalyze the direct conversion of tyrosine to PHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

The term "P-450/P-450 reductase system" refers to a protein system responsible for the catalytic conversion of cinnamic acid to PHCA. The P-450/P-450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to PHCA, whereas the term "P-450/P-450 reductase system" will refer to a specific binary protein system that has cinnamate 4-hydroxylase activity.

The term "PAL/TAL activity" or "PAL/TAL enzyme" refers to a protein which contains both PAL and TAL activity. Such a protein has at least some specificity for both tyrosine and phenylalanine as an enzymatic substrate.

The term "catalytic efficiency" will be defined as the $k_{cat}/K_M$ of an enzyme. "Catalytic efficiency" will be used to quantify the specificity of an enzyme for a substrate.

The term "$k_{cat}$" is often called the "turnover number". The term "$k_{cat}$" is defined as the maximum number of substrate molecules converted to products per active site per unit time, or the number of times the enzyme turns over per unit time. $k_{cat}=V_{max}/[E]$, where [E] is the enzyme concentration (Ferst In *Enzyme Structure and Mechanism*, $2^{nd}$ ed.; W.H. Freeman: New York, 1985; pp 98–120).

The term "aromatic amino acid biosynthesis" means the biological processes and enzymatic pathways internal to a cell needed for the production of an aromatic amino acid.

The term "fermentable carbon substrate" refers to a carbon source capable of being metabolized by host organisms of the present invention and particularly carbon sources selected from the group consisting of monosaccharides, oligosaccharides, polysaccharides, one-carbon substrates and/or mixtures thereof.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method are KTUPLE 1, GAP PENALTY= 3, WINDOW=5 and DIAGONALS SAVED=5.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The invention encompasses more than the specific exemplary sequences because it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

Suitable nucleic acid fragments (isolated polynucleotides of the present invention) encode polypeptides that are at least about 70% identical, preferably at least about 80% identical to the amino acid sequence reported herein. Preferred nucleic acid fragments encode amino acid sequences that are about 85% identical to the amino acid sequence reported herein. More preferred nucleic acid fragments encode amino acid sequences that are at least about 90% identical to the amino acid sequence reported herein. Most preferred are nucleic acid fragments that encode amino acid sequences that are at least about 95% identical to the amino acid sequence reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptide as set forth in SEQ ID NO:25. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. Expression may be "induced" by providing a specific inducing agent to a cell that results in hightened expression of a gene. In the context of the present invention expression of the instant TAL genes are induced in by the presence of tyrosine.

"Antisense inhibition" refers to the production of antisense RNA transcripts capable of suppressing the expression of the target protein.

"Overexpression" refers to the production of a gene product in transgenic organisms that exceeds levels of production in normal or non-transformed organisms.

"Co-suppression" refers to the production of sense RNA transcripts capable of suppressing the expression of identical or substantially similar foreign or endogenous genes (U.S. Pat. No. 5,231,020).

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Gene Involved in PHCA Production in *T. cutaneum*

The gene encoding the TAL activity of the present invention was isolated from the yeast *Trichosporon cutaneum*, ATCC No. 58094. This TAL enzyme was induced by the presence of tyrosine, but not phenylalanine. The yeast *Trichosporon cutaneum* catabolizes L-tyrosine aerobically in an initial attack by an ammonia lyase to form p-hydroxycinnamic acid (Sparnins et al., *J. Bacteriol.* 138:425(1979)). With subsequent hydration and aldol cleavage, p-hydroxybenzaldehyde is produced, so that degradation then proceeds by way of p-hydroxybenzoate, protocatechuate, hydroxyquinol, and maleylacetate which is a substrate for the energy generating TCA cycle.

Sequence Identification

The nucleotide sequence isolated from *T. cutaneum* that encodes the TAL enzyme of this invention is given as SEQ ID NO:24. Comparison of this nucleotide base and the deduced amino acid (SEQ ID NO:25) sequences to public databases reveals that the most similar known sequences are about 48% identical to the amino acid sequence reported herein over length of 689 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 70%–80% identical to the sequences herein, where about 88%–85% is suitable, 85%–90% is preferred and 90%–95% is most preferred. Similarly, preferred TAL encoding nucleic acid sequences corresponding to the instant sequence are those encoding active proteins and which are at least about 70%–80% identical to the sequences herein, where about 88%–85% is suitable, 85%–90% is preferred and 90%–95% is most preferred.

Isolation of Homologs

The nucleic acid fragment of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci.* USA 82, 1074, (1985; or strand displacement amplification (SDA), Walker, et al., *Proc. Natl. Acad. Sci. U.S.A.*, 89: 392, (1992)).

For example, genes encoding similar proteins or polypetides to those of the instant invention could be isolated directly by using all or a portion of the instant nucleic acid fragment as DNA hybridization probes to screen libraries from any desired bacteria using methodology well known to those skilled in the art. Specific oligonucleotide probes based upon the instant nucleic acid sequence can be designed and synthesized by methods known in the art (Maniatis, supra). Moreover, the entire sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequence may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragment, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequence. Using commercially available 3' RACE or 5' RACE systems (Life Technologies, Rockville, Md.), specific 3' or 5' cDNA fragments can be isolated (Ohara et al., *PNAS USA* 86:5673 (1989); Loh et al., *Science* 243:217 (1989)).

Alternatively the instant sequence may be employed as an hybridization reagent for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kDal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Recombinant Expression—Microbial

The gene and gene product of the instant sequence may be produced in heterologous host cells, particularly in the cells of microbial hosts.

Microbial expression systems and expression vectors containing regulatory sequences that direct high level expression of foreign proteins are well known to those skilled in the art. Any of these could be used to construct chimeric genes for production of the gene product of the instant sequence. These chimeric genes could then be introduced into appropriate microorganisms via transformation to provide high level expression of the enzyme.

Accordingly, it is expected for example that introduction of a chimeric gene encoding the instant microbial enzyme under the control of the appropriate promoters will demonstrate increased production of PHCA. It is contemplated that it will be useful to express the instant gene both in natural host cells as well as heterologous hosts. Introduction of the present gene into the native host will result in elevated levels of existing production of PHCA. Additionally, the instant gene may also be introduced into non-native host bacteria where there are advantages to manipulate the PHCA production that are not present in the organism from which the instant gene is directly isolated.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant TAL gene in the desired host cell are numerous and familiar to those skilled in the art. Virtually any promoter capable of driving this gene is suitable for the present invention including, but not limited to: CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred heterologous host cells for expression of the instant gene and nucleic acid fragment are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragment. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of host strains include but are not limited to bacteria, such as the enteric bacteria (*Escherichia*, and *Salmonella* for example) as well as *Bacillus, Acinetobacter, Streptomyces, Methylobacter*, and *Pseudomona; Cyanobacteria*, such as *Rhodobacter* and *Synechocystis*; yeasts, such as *Saccharomyces, Zygosaccharomyces, Kluyveromyces, Candida, Hansenula, Debaryomyces, Mucor, Pichia* and *Torulopsis*; filamentous fungi such as *Aspergillus* and *Arthrobotrys*; and algae such *Spirulina, Haemotacoccus*, and *Dunalliela*. The TAL gene of the present invention may be produced in these and other microbial hosts to prepare large, commercially useful amounts of PHCA.

Pathway Engineering

Knowledge of the sequence of the TAL gene will be useful in manipulating the PHCA biosynthetic pathways in any organism having such a pathway. Moreover, introducing the TAL gene into any organism with the endogenous or engineered ability to produce tyrosine will enable PCHA production from a carbon source such as glucose. Methods of manipulating genetic pathways are common and well known in the art. Selected genes in a particularly pathway may be upregulated or down regulated by variety of methods. Additionally, competing pathways in an organism may be eliminated or sublimated by gene disruption and similar techniques.

Once a key genetic pathway has been identified and sequenced, specific genes may be upregulated to increase the output of the pathway. For example, additional copies of the targeted gene may be introduced into the host cell on multicopy plasmids such as pBR322. Alternatively the target gene may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods for gene down regulation is targeted gene disruption where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al. *J. Bacteriol.* 171:4617–4622 (1989); Balbas et al. *Gene* 136:211–213 (1993); Gueldener et al. *Nucleic Acids Res.* 24:2519–2524 (1996); and Smith et al. *Methods Mol. Cell. Biol.* 5:270–277(1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36: 227 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the PHCA producing enzyme pathway by any one of the methods described above. For example, it would be advantageous to maximize the production of tyrosine from glucose by down-regulating competing pathways, such as the production of phenylalanine.

Industrial Production

Where commercial production of PHCA is desired, a variety of culture methodologies may be applied. For example, large-scale production of a specific gene product overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of PHCA may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Alternatively, the present invention provides for the production of PHCA in plant cells containing the TAL gene. The nucleic acid fragment of the instant invention may be used to create transgenic plants having the ability to express the microbial gene for the production of PHCA. Preferred plant hosts will be any variety that will support a high production level of PHCA or PHCA-glucoside conjugate. Suitable green plants will include, but are not limited to: soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa, L*), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Overexpression of the PHCA may be accomplished by first constructing a chimeric gene of the present invention in which the coding regions are operably linked to promoters capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The instant chimeric gene may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequence or the present invention should be capable of promoting expression of the present gene product. High level plant promoters that may be used in this invention, for example, include the promoter of the small subunit (ss) of the ribulose-1,5-bisphosphate carboxylase from soybean (Berry-Lowe et al., *Journal of Molecular and Applied Genetics*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pp 29–38; Coruzzi, G. et al., *J. Biol. Chem.*, 258:1399 (1983), and Dunsmuir, P. et al., *Journal of Molecular and Applied Genetics*, 2:285 (1983)).

Plasmid vectors comprising the instant chimeric gene can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98, 503, (1975)), Northern analysis of mRNA expression (Kroczek, *J. Chromatogr. Biomed. Appl.*, 618 (1–2) 133–145 (1993)), Western analysis of protein expression, or phenotypic analysis.

For some applications it will be useful to direct the instant protein to different cellular compartments. It is thus envisioned that the chimeric gene described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research* 27(4): 1056–1062 (1999)); site directed mutagenesis (Coombs et al., *Proteins* (1998), 259–311, 1 plate, Editor(s): Angeletti, Ruth Hogue, Publisher: Academic, San Diego, Calif.), and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequence of the present invention may be mutated and screened for altered or enhanced activity by this method. The sequences should be double stranded and can be of various lengths ranging from 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocols (Manatis supra).

Furthermore, a hybrid protein can be assembled by fusion of functional domains using the gene shuffling (exon shuffling) method (Nixon et al., *PNAS*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

DESCRIPTION OF PREFERRED EMBODIMENTS

The present invention comprises an enzyme which can be used for the production of PHCA directly from tyrosine. The instant gene of this invention encodes a protein having tyrosine ammonium lyase (TAL) activity. A TAL activity will convert tyrosine directly to PHCA with no intermediate step according to the following scheme:

The *T. cutaneum* strain (ATCC No. 58094) from which the TAL gene of this invention was isolated was discovered by screening a variety of microbial strains for PAL and TAL activity, which was induced by tyrosine. The TAL enzyme was isolated and purified using a variety of chromatographic techniques. The N-terminus and an internal fragment of the purified enzyme were sequenced to enable primers to be developed for PCR cloning of the genomic sequence of *T. cutaneum* tal. These primers were used in Touch Down and Ramped Annealing PCR, using both genomic DNA and cDNA as template to clone a portion of the TAL cDNA. A consensus sequence of the clones obtained from these two methods contained an intron sequence due to genomic DNA or non-processed mRNA contamination. Primers designed against the consensus sequence were used to generate the full length TAL cDNA sequence using 5' RACE and 3' RACE cloning of the TAL cDNA. The resulting tat sequence has a high degree of homology to known PAL genes from a variety of organisms. The TAL protein sequence (SEQ ID NO:25) had a relatively low homology (28% identity) with the protein sequence of the TAL from *Rhodobacter capsulatus* (Kyndt et al., *FEBS Letters* 512:240–244 (2002)). After removal of the intron, the TAL gene was cloned into the vector pYES2.0 under the control of the yeast GAL1 promotor and successfully expressed in the yeast *Saccharomyces cerevisiae*. The TAL gene was also expressed in the bacterium *Escherichia coli*.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are Well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

The meaning of abbreviations is as follows: "s" means second(s), "min" means minute(s), "h" means hour(s), "psi" means pounds per square inch, "nm" means nanometers, "d" means day(s), "$\mu$L" means microliter(s), "mL" means milliliter(s), "L" means liter(s), "mm" means millimeter(s), "nm" means nanometers, "mM" means millimolar, "M" means molar, "mmol" means millimole(s), "$\mu$mole" means micromole(s)", "g" means gram(s), "$\mu$g" means microgram(s) and "ng" means nanogram(s), "U" means units, "mU" means milliunits and "U mg$^{-1}$" means units per mg, "OD" means optical density, "kDa" means kilodaltons, "g" means the gravitation constant.

Example 1

Screening of Various Microbial Strains Containing PAL and TAL Activity

The purpose of this Example was to screen a variety of microbial strains for PAL/TAL activity in order to identify a strain with an enzyme that had a higher TAL than PAL activity.

Cell Growth and Tyrosine Induction

The yeast strains: *Rhodotorula rubra* (ATCC No. 889), *Saccharomycopsis fibuligera* (ATCC No. 2080), *Rhodosporidium toruloides* (ATCC No. 10788), *Sporidobolus pararoseus* (ATCC No. 11386), *Sporidiobolus ruinenii* (ATCC No. 20489), *Rhodotorula graminis* (ATCC No. 20804), *Rhodotorula minuta* (ATCC No. 32769), *Trichosporon cutaneum* (ATCC No. 46446), and *Trichosporon cutaneum* (ATCC No. 58094) were obtained from the American Type Culture Collection (ATCC, Manassas, Va.). These yeast strains were streaked out from glycerol stock onto nutrient agar plates and grown at 30° C. Single colonies were then selected and transferred to 50 mL of Dagley's medium (Sparnins, et al, *J. Bact.* 138:425–430 (1979)) supplemented with 0.1 g/L of tyrosine, phenylalanine or succinate. Alternatively, a minimal media, consisting of 1.61 g/L of $K_2HPO_4$, 5.55 g/L of $KH_2PO_4$, 0.1 g/L $MgSO_4$, 0.01 g/L of biotin, with a pH of 6.2 and supplemented with 0.5 g/L of tyrosine, was used. The cells were grown up at 30° C. on a shaker at ~250 rpm to an OD between 1.0 and 2.0 at 600 nm. The cells were then pelleted by centrifugation and resuspended in 1.0 mL of 50 mM Tris-HCl buffer, pH 8.5.

Preparation of Cell Free Extracts

The cells were washed and then resuspended in 50 mM Tris-HCl buffer, pH 8.5, containing 1.0 $\mu$g/mL of both leupeptin and pepstatin A, 0.5 mM of PMSF (phenylmethylsulfonyl fluoride) and a small amount of DNase. The cells were then passed twice through a French Pressure Cell at 18,000 psi and the debris was removed by centrifugation at 38,720×g for 20 min at 4° C. The supernatant was then used as the crude cell free extract for enzyme assays.

Protein Assay

Protein concentrations were determined using the Bradford method (Anal. Biochem. 72:248–254 (1976)). The Coomassie solution was mixed with varying amounts of the cell free extracts and the OD at 595 nm was measured.

PAL and TAL Assays

The reaction was initiated by the addition of enzyme to 50 mM Tris-HCl (pH 8.5) containing 1.0 mM L-phenylalanine or L-tyrosine and the reaction was followed spectrophotometrically by monitoring the absorbance of the product. For PAL activity, cinnamate formation was monitored at 290 nm using a molar extinction coefficient of 9000 cm-1. One unit of activity deaminates 1.0 $\mu$mol of phenylalanine to cinnamate in one min. For TAL activity, PHCA formation was monitored at 315 nm (extinction coefficient of 10,000 cm-1). One unit of activity deaminates 1.0 $\mu$mol of tyrosine to PHCA in one min.

Enzymatic Kinetic Assays

The apparent $V_{max}$ and $K_M$ values were determined using the cell-free extracts from cells grown in Dagley's medium in the presence of 2.0 mM tyrosine.

Results

The specific activity of PAL, TAL and the PAL/TAL ratio in cell-free extracts from various microbial strains are shown in Table 1. The results indicated that among the microbial strains tested, addition of tyrosine to *T. cutaneum* ATCC No. 58094 induced PAL and TAL activities. In addition, the *T. cutaneum* enzyme had high TAL activity with a PAL/TAL ratio of 0.73. The enzyme kinetic studies on the PAL and TAL enzymes in these microorganisms also revealed that $V_{max}$ for TAL was highest in *T. cutaneum* ATCC No. 58094, compared to the other microorganisms, as shown in Table 2.

TABLE 1

PAL/TAL Ratio in Cell-Free Extracts of Various Microorganisms Induced by Tyrosine

| ATCC Number | Microoganism Name | Specific Activity PAL (U/mg) | TAL (U/mg) | PAL/TAL Ratio |
|---|---|---|---|---|
| 889 | R. rubra | 0.1226 | 0.0392 | 3.13 |
| 2080 | S. fibulige | 0.0073 | 0.0018 | 4.06 |
| 10788 | R. toruloides | 0.0930 | 0.0352 | 2.64 |
| 11386 | S. pararoseus | 0.1094 | 0.0276 | 3.97 |
| 20489 | S. ruinenii | 0.0154 | 0.0039 | 3.91 |
| 20804 | R. graminis | 0.1932 | 0.0467 | 4.14 |
| 32769 | R. minuta | 0.0575 | 0.0135 | 4.25 |
| 58094 | T. cutaneum | 0.0355 | 0.0488 | 0.73 |

TABLE 2

PAL/TAL Enzyme Kinetic Constants

| ATCC # | Name | PAL Vmax (U/mg) | Km (mM) | Vmax/Km | TAL Vmax (U/mg) | Km (mM) | Vmax/Km | Ratio PAL/TAL |
|---|---|---|---|---|---|---|---|---|
| 889 | R. rubra | 0.169 | 0.446 | 0.379 | 0.033 | 0.220 | 0.150 | 2.52 |
| 2080 | S. fibulige | 0.011 | 0.467 | 0.023 | 0.002 | 0.156 | 0.013 | 1.74 |
| 10788 | R. glutinis | 0.178 | 0.518 | 0.344 | 0.033 | 0.209 | 0.156 | 2.20 |
| 11386 | S. pararoseus | 0.179 | 0.507 | 0.353 | 0.033 | 0.327 | 0.100 | 3.55 |
| 20489 | S. ruineniae | 0.024 | 0.389 | 0.061 | 0.004 | 0.264 | 0.015 | 4.09 |
| 20804 | R. graminis | 0.239 | 0.448 | 0.534 | 0.044 | 0.154 | 0.286 | 1.87 |
| 32769 | R. minuta | 0.083 | 0.584 | 0.142 | 0.011 | 0.212 | 0.051 | 2.79 |
| 46446 | T. cutaneum | 0.128 | 49.6 | 0.003 | 0.013 | 13.1 | 0.001 | 2.64 |
| 58094 | T. cutaneum | 0.777 | 2.33 | 0.333 | 0.179 | 0.431 | 0.415 | 0.80 |

Example 2

Induction of Tyrosine Ammonia Lyase Activity in *T. cutaneum*

The purpose of this Example was to demonstrate that expression of the TAL enzyme was induced when *T. cutaneum* was grown in the presence of tyrosine.

*T. cutaneum* was cultured in the presence of tyrosine, phenylalanine or succinate, as described in Example 1. Cell free extracts of *T. cutaneum* were obtained as described in Example 1 and were analyzed using SDS-PAGE (Sodium Dodecyl Sulfate-Polyacrylamide Gel Electrophoresis). As shown in FIG. 1, SDS-PAGE analysis demonstrated that there was a specific band (77.5 kDa), which was designated as tyrosine ammonia lyase (TAL), that responded to tyrosine induction. In FIG. 1, lane A is the cell free extract obtained with succinate induction, lane B is the cell free extract obtained with phenylalanine induction, and lane C is the cell free extract obtained with tyrosine induction. The molecular weight markers (for alkaline conditions) in the first lane are phosphorylase B (94 kDa), albumin (67 kDa), ovalbumin (43 kDa), carbonic anhydrase (30 kDa), trypsin inhibitor (20.1 kDa) and alpha-lactalbumin (14.4 kDa).

Example 3

Purification and Characterization of TAL from *T. cutaneum*

The purpose of this Example was to purify the TAL enzyme from *T. cutaneum* using anion exchange chromatography, hydrophobic interaction chromatography and gel filtration chromatography. PAGE was used check the purity of the enzyme.

Growth Conditions

*Trichosporon cutaneum* ATCC No. 58094 was first streaked out from glycerol stocks onto nutrient agar plates, followed by growth in Dagley's medium in the presence of tyrosine at 30° C. The cells were harvested when growth reached an OD of about 0.6 at 600 nm. The yield of the cells was approximately 1.0 g wet weight/L. All subsequent extraction and purification procedures were carried out at 4° C.

Preparation of Cell Free Extracts

The harvested cell pellet was washed once with 100 mM, pH 8.5 Tris-HCl and suspended in 100 mM, pH 8.5 Tris-HCl buffer containing 1.0 mM EDTA to a concentration of 1.0 g wet weight of cells/mL. A mini tablet of proteinase inhibitor mix (Complete mini, Roche Molecular Biochemicals, Indianapolis, Ind.) was then added along with leupeptin and pepstatin A, both at 1.0 μg/mL, bestatin, 50 μg/mL, and a small amount of DNase. The cells were passed twice through a French Pressure cell at approximately 18,000 psi and the debris was removed by centrifugation (38,720×g for 20 min).

Anion Exchange Chromatography

The crude cell extract was applied to an 20 mm×165 mm HQ column (Perceptive Biosystems, Farmingham, Mass.) which had been equilibrated with 10 mM Tris-HCl buffer, pH 8.5, containing 0.2 mM EDTA. After washing with about 2 column volumes of the equilibrating buffer, the column was eluted with a gradient from 100% of eluting buffer (10 mM Tris-HCl buffer, pH 8.5 containing 0.5 M NaCl and 0.2 mM EDTA) to 50% of equilibrating buffer and eluting buffer over 10 column volumes, at a flow rate of 25 mL/h, while 10 mL fractions were collected. Active fractions (nos. 18–22, containing 215 mg protein) were pooled and concentrated using a Centriprep YM-50 centrifugal filter unit (Millipore, Bedford, Mass.).

Hydrophobic Interaction Chromatography (HIC)

HIC was carried out on a 20 mm×167 mm, 50 μm PE column (Perceptive Biosystems, Farmingham, Mass.) at a flow rate of 30 mL/min. The starting buffer (buffer A) was 1.0 M $(NH_4)_2SO_4$ in 10 mM, pH 8.5 Tris-HCl with 1.0 mM EDTA and the eluting buffer (buffer B) was 10 mM, pH 8.5 Tris-HCl with 1.0 mM EDTA. The column was equilibrated for 2 column volumes and washed with 2 column volumes of buffer A after sample injection. A gradient of 100% of buffer A to 100% of buffer B over 10 column volumes was then applied. The column was cleaned with 2 column volumes of buffer B and then re-equilibrated with buffer A for 2 column volumes. Protein was monitored at 280 nm and 10 mL fractions were collected on ice. Samples, containing up to 50 mg of protein (12% of the column's capacity of 420 mg), were adjusted to about 1.0 M $(NH_4)_2SO_4$ by the addition of a saturated ammonium sulfate solution. Active fractions (nos. 12 to 17) were pooled and concentrated using a Centriprep YM-50 centrifugal filtration unit.

Gel Filtration (GF) Chromatography

Gel filtration was carried out on a 10 mm×305 mm, Superdex 200 HR column at flow rate of 1.0 mL/min. The buffer was 100 mM, pH 8.5 Tris-HCL containing 0.2 M NaCl and 1.0 mM EDTA. The column was run for one column volume with protein monitored at 280 nm. Fractions (0.5 mL) were collected on ice after 0.25 column volumes were passed through the column. Samples (100 μL, up to 10 mg of protein) were collected. The column was run five times and fractions collected. The fractions with highest activity were pooled, concentrated and desalted using a Centricon YM-50 centrifugal filtration unit (Millipore).

PAGE and Isoelectric Focusing (IEF) Electrophoresis Analysis

For analysis using the Phast-Gel System (Amersham Pharmacia Biotech, Piscataway, N.J.), 4.0 μg of protein was used per lane. The PAL/TAL standard used was a purified sample. Molecular weight standards were obtained from Amercham Pharmacia Biotech. Low molecular weight markers were used as standards for the 12.5% SDS gel and high molecular weight markers for the 8–25% native gel. Low pI standards and purified PAL/TAL enzyme were used as standards for the pI 4–6.5 IEF gel.

Protein Assay

Protein concentrations were measured as described in Example 1.

Results

As shown in Table 3, a significant increase in specific activity was obtained following purification of TAL using the chromatographic techniques described above. The largest increase was obtained using HIC and GF, which both gave about a 14-fold increase in specific activity.

TABLE 3

Purification of TAL Enzyme

| Sample | Vol (mL) | Protein (mg/mL) | Total Protein (mg) | Activity (U/L) | Total Activity (Units) | Specific Activity (U/mg) | Yield (%) | Purification (Fold) |
|---|---|---|---|---|---|---|---|---|
| Crude Extract | 7.5 | 28.62 | 214.7 | 0.68 | 5.06 | 0.0236 | 100 | 1 |
| Anion Exchange | 5.8 | 2.18 | 12.6 | 0.22 | 1.24 | 0.0982 | 25 | 4.16 |
| HIC | 1.1 | 2.54 | 2.8 | 0.81 | 0.89 | 0.3184 | 18 | 13.51 |
| GF | 0.4 | 2.16 | 0.84 | 0.72 | 0.28 | 0.3313 | 6 | 14.05 |

Figure 2:
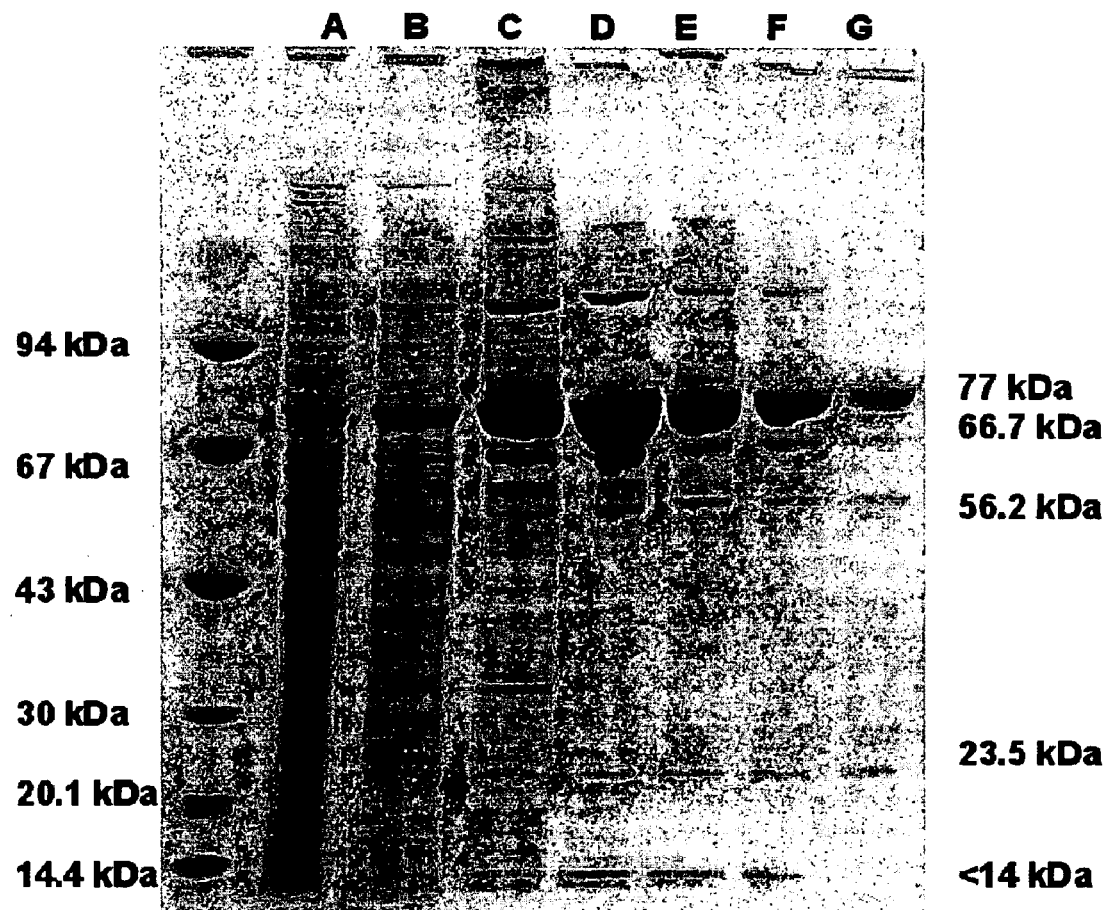
FIG. 2 is a gel image of the polyacrylamide gel electrophoresis of the purified TAL from *T. cutaneum*.

Similar results were obtained using PAGE to determine the purity of the TAL enzyme, as shown in FIG. 2. In FIG. 2, the lanes are as follows: (A) Cell-free extract (20 μg), (B) Anion exchange chromatography sample (20 μg), (C) Hydrophobic interaction chromatography sample (20 μg), (D) Gel filtration chromatography sample (20 μg), (E) Gel filtration chromatography sample (10 μg), (F) Gel filtration chromatography sample (5 μg) and (G) the purified PAL enzyme from *R. glutinis* as a reference. Molecular weight markers for alkaline conditions were phosphorylase B (94 kDa), albumin (67 kDa), ovalbumin (43 kDa), carbonic anhydrase (30 kDa), trypsin inhibitor (20.1 kDa) and alpha-lactalbumin (14.4 kDa).

Example 4

Sequencing of the N-terminus and Internal Fragments of the Purified TAL Enzyme from *T. cutaneum*

The purpose of this example was to obtain the N-terminal and internal peptide sequences of the TAL enzyme to enable primers to be developed for PCR cloning of the genomic DNA sequence of *T. cutaneum* tal.

SDS-PAGE

The purified TAL enzyme from *T. cutaneum*, obtained from gel filtration purification (as described in Example 3), was prepared in 4× protein sample buffer (Novagen, Madison, Wis.) containing 10% β-mercaptoethanol and heated at 80° C. for 1.0 min. The protein sample (4.0 to 10.0 μg per lane, four lanes in total) was applied to a 4–12% gradient Bis-Tris Gel (Novagen, Madison, Wis.) and electrophoretically separated using an applied voltage of 100 V for about 2 h.

Electrotransfer and Blotting

Electrotransfer and blotting of the protein to a PVDF (polyvinylidene fluoride) membrane (Bio-Rad, Hercules, Calif.) was carried out using an electrophoretic transfer cell (Bio-Rad). Three layers of Whatman filter paper in the size of the gel (6×7 cm) were soaked in Electrotransfer buffer (10 mM Tris base, 100 mM glycine and 10% methanol). The PVDF membrane was pre-wet in 100% methanol for at least 10 s and then immersed in the transfer buffer for at least 5 min. The transfer sandwich was assembled according to the manufacture's procedures. The blotting was carried out at 80 mA for about 90 min.

Protein Sequencing

The peptide bands on the PVDF membrane were visualized by staining with amido black. The bands of interest were excised from the PVDF membrane for N-terminal sequencing at the DuPont Peptide Sequencing Facility. To further confirm the sequence, separate PVDF membrane blots containing the gel filtration purification product from Example 3 were also submitted for sequence analysis at the Wistar Protein Microchemistry/MS facility (The Wistar Institute, Philadelphia, Pa.).

Results

As shown in Lane F of FIG. 2, 5 peptide bands with molecular weights of 77.5, 62, 56, 23.5 and 14 kDa were detected after SDS-PAGE separation of the sample from gel filtration purification. All 5 peptides were submitted for N-terminal sequencing at the DuPont Sequencing Facility. The N-terminal sequence of 4 of these peptides (the 77.5, 62, 23.5 and 14 kDa peptides) were obtained. Three of these peptides, specifically the 77.5, 23.5 and 14 kDa peptides, had similar N-terminal sequences, suggesting that the smaller ones were degradation products of the major peptide component (77.5 kDa). The N-terminal sequence of the 77.5 kDa peptide was designated as SEQ ID NO:1, and referred to as the N-terminal sequence.

Since the combined molecular weight of the 62 kDa and the 14 kDa peptides, and the 56 kDa and the 23.5 kDa peptides roughly equals the molecular weight of the main 77.5 kDa peptide, it is likely that the 62 kDa and the 56 kDa peptides were also degradation products. The N-terminal sequence of the 62 kDa peptide showed significant similarity to other PAL enzymes in the database. This sequence was designated as SEQ ID NO:2, and referred to as the internal sequence because this peptide is likely the degradation product of the 77.5 kDa peptide without the 14 kDa N-terminal portion.

The N-terminal sequence obtained for the 77.5 kDa peptide by the Wistar Protein Microchemistry/MS facility was identical to that obtained by the DuPont Sequencing Facility.

Example 5

Cloning of TAL cDNA from *T. cutaneum*

This Example outlines experiments leading to the sequencing of the *T. cutaneum* TAL cDNA to be used for expression in yeast. From the N-terminal and internal peptide sequences generated in Example 4, primers were designed to perform Touch Down PCR and Ramped Annealing PCR, aimed at cloning a portion of the TAL cDNA. The consensus sequence of the clones obtained from Touch Down and Ramped Annealing PCR contained an intron sequence due to genomic DNA or, non-processed mRNA contamination. Primers designed against the consensus sequence were used to generate the full length TAL cDNA using the RACE PCR method.

Preparation of Genomic DNA and RNA Using TRIZOL-Reagent

*T. cutaneum* (ATCC No. 58094) was cultured as described in Example 1. The cells were centrifuged at 9000×g at 4° C. and the resulting cell pellet was resuspended in 2.0 mL of the Trizol Reagent (Life Technologies, Rockville, Md.). The mixture was homogenized and the resuspended cells were distributed in 1.0 mL aliquots. After a 5 min incubation at room temperature, 0.5 mL of chloroform was added to each sample. Then, each sample was shaken vigorously by hand for 15 s and incubated for another 3 min at room temperature. The samples were then centrifuged in a bench top centrifuge at 14,000 rpm at 4° C. for 15 min. The upper aqueous phases were saved for RNA isolation, while the interphase and lower organic phase from each sample were used for DNA preparation.

To each tube containing the DNA, 0.5 mL of 100% ethanol was added and the tubes were mixed by pipetting. After a 3 min incubation at room temperature, the tubes were centrifuged at 14,000 rpm and 4° C. for 5 min. The supernatant was discarded and the pellets were resuspended in 1.0 mL of sodium citrate (0.1 M in 10% ethanol). After a 30 min incubation at room temperature, the samples were washed twice, as described above and 1.2 mL of 75% ethanol was added to the pellets and the samples were incubated for 10 min at room temperature. The pellets were washed once more and were allowed to air-dry for 10 min. Then, NaOH (200 μL of an 8 mM solution) was added and the pellets were allowed to dissolve at room temperature for two days.

Isopropyl alcohol was added to the upper aqueous phase containing RNA, the sample was mixed and then, incubated for 10 min at room temperature. The samples were centrifuged at 9000×g for 30 min. The RNA pellets were washed with 75% ethanol, made with water treated with 0.1% diethyl pyrocarbonate (DEPC), followed by centrifugation at 7500×g at 4° C. for 5 min. The RNA pellets were air-dried for 15 min and then dissolved in 1.0 mL DEPC-treated water.

Purification of mRNA from Total RNA

The mRNA was purified from the total RNA preparation using the Oligotex mRNA miniprep kit (Qiagen, Valencia, Calif.) according to the protocol provided by the manufacture. The volume of the total RNA sample was adjusted to 250 μL with RNase-free H$_2$O. OBB buffer (250 μL), consisting of 20 mM Tris-HCl, pH 7.5, 1 M NaCl, 2 mM EDTA, and 0.2% SDS, from Qiagen and Oligotex-suspension (15 μL) were added to each sample and the samples were mixed thoroughly. The samples were incubated for 3 min at 70° C. in a heating block and then left at room temperature for 10 min. The Oligotex-mRNA complex was pelleted by centrifugation at 15,000×g for 2 min. The supernatant was carefully removed. The Oligotex-mRNA complex was resuspended in 400 μL of OW2 buffer (Qiagen), transferred to a small spin column, centrifuged for 1 min, and washed twice. The spin column was placed into a 70° C. heating block and 50 μL of OEB buffer (Qiagen), preheated to 70° C., was pipetted into each sample. After incubating for 1 min, the column was centrifuged at 15,000×g for 1 min to recover the mRNA.

Reverse Transcription of TAL mRNA

The Superscript™ First-Strand Synthesis System from Life Technologies was used for reverse transcription. The poly A(+) RNA sample (8 μL of a 0.3 mg/mL solution), 1 μL of 10 mM dNTP mix and 1 μL of oligo(dT) at 0.5 mg/mL were mixed together, heated to 65° C. for 5 min and chilled on ice for 1 min. To this mixture were added the following reagents from the kit, 2 μL of 10×RT buffer, 4 μL of 25 mM MgCl$_2$, 2 μL of 0.1 M DTT, and 1 μL of RNase inhibitor. The reaction mixture was incubated at 42° C. for 2 min. Then, 1 μL of Superscript II reverse transcriptase was added and the mixture was incubated for 50 min at 42° C. The reaction was terminated by incubation at 70° C. for 15 min. RNA was removed by the addition of 1 μL of RNase H followed by incubation at 37° C. for 20 min.

PCR Amplification of tal from *T. cutaneum*

Based on the N-terminal and internal sequences generated in Example 4, the primers given in Table 4 were designed for PCR cloning of the 5'-end region of the tal of *T. cutaneum*, either by direct PCR amplification using genomic DNA as template or by RT-PCR (reverse transcriptase-PCR) amplification using poly A(+) RNA as template. Both Touch Down PCR and Ramped Annealing PCR methods were used, as described below.

TABLE 4

Primers for Cloning of the 5'-End Region of tal from *T. cutaneum*

| Name | Sequence (5'-3') | SEQ ID NO: |
|---|---|---|
| Nterm3-17Af | GAGACCAACGTCGCCAAGCCCGCCTCGAC CAAGGCCATGAACGC | 3 |
| Nter3-17Bforw | GAGACCAACGTCGCCAAGCCCGCCAGCAC CAAGGCCATGAACGC | 4 |
| Int-14forw | GCCGACACCCGCACCTCGGACACBGAGGC | 5 |
| Int18-9rev | GGCAATCTGGAGGGCCTCVGTGTC | 6 |
| 86Int15-4rev | GTCCTGGTCGGCGAGGAGCTCGGGCTCCT CGTG | 7 |
| 101Int12-4rev | GCCTCGAGCTGGGGGCCRATCCACTG | 8 |

Touch Down PCR Amplification of tal Using Genomic or cDNA Template

Touch Down PCR (Dan, et al. *Nucleic Acids Res.* 19:4008 (1991)) was used to amplify tal using either genomic or cDNA template as follows. One microliter of either genomic DNA or cDNA from *T. cutaneum* was used as template for amplification with HotStartTaq Mastermix from Qiagen. The reaction mixture had a volume of 50 μL and contained 0.1 µM of each primer (Table 4), 1.5 mM of MgCl$_2$, and 200 µM of dNTP. PCR buffer (10×) was added to a 1× final concentration. The PCR conditions were as follows: 15 min at 94° C., followed by 30 cycles of PCR with 30 slat 94° C., 20 s at the annealing temperature and 1 min at 72° C. The annealing temperature started at 94° C. and decreased stepwise to 74° C. in 4° C. steps every two cycles. Then it was decreased to 60° C. in 2° C. steps every two cycles. Finally it was set at 55° C. for 5 cycles. The PCR product was then used as template at the same conditions for a second round of PCR, using the same set of primers.

A band of the expected size was detected by gel electrophoresis in amplifications using the following primer combinations: SEQ ID NOs:3 and 6, 3 and 7, 3 and 8, 4 and 7, and 4 and 8. Thus, primers SEQ ID NOs:3 and 8 were used to amplify chromosomal DNA using the above conditions. The PCR product was then used as template for a further round of amplification, using the following primers: SEQ ID NOs:3 and 6, 3 and 7, 3 and 8, and 5 and 7. The annealing temperature for this round was set at 55° C. for 20 s for all 30 cycles. Analysis of each reaction product using gel electrophoresis showed a very strong band with the expected size. Aliquots of these PCR reactions (4 µL) were ligated into pCR2.1 cloning vector according to the manufacturer's protocol (TOPO-TA-cloning from Invitrogen, Carlsbad, Calif.) and were transformed into TOPO10 Chemically Competent *E. coli* cells (Invitrogen). White colonies were picked, and the plasmid DNAs were isolated and sequenced by the DuPont Sequencing Facilities. The resulting sequences were used to construct the consensus sequence, as described below.

Ramped Annealing PCR Amplification of tal

Ramped Annealing PCR (Andrea, et al. *Bio Techniques* 29:1182–1186 (2000)) was also used for amplification with both genomic and the cDNA template. In this method, the annealing temperature was linearly decreased from 94° C. to 55° C. over 10 minutes in each of the 30 cycles of PCR. All the other conditions were the same as described for Touch Down PCR.

The following primer combinations SEQ ID NOs:4 and 7, 5 and 7, and 5 and 8 generated a product with the expected size with cDNA as a template. Primer combinations SEQ ID NOs:5 and 7, and 5 and 8 also generated a product with the expected size with genomic DNA as template. These PCR products were used as templates for a second round of amplification where the annealing temperature was fixed at 55° C. for all 30 cycles. All of the second round products were cloned into pCR2.1 as described above and 7 positive clones were subjected to sequence analysis.

A consensus sequence of 1095 bp was compiled from the positive clones obtained using the Touch Down and Ramped Annealing PCR methods described above. Analysis of the consensus sequence, given as SEQ ID NO:9, showed that it was the reverse complement of the coding sequence. SEQ ID NO:9 was analyzed for similarity to all publicly available DNA sequences by conducting a BLAST (Basic Local Alignment Search Tool; Altschul, S. F., et al., (1993) *J. Mol Biol*. 215:403–410; see also www.ncbi.nlm.nih.gov/BLAST/) search for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases) using the BLASTN algorithm provided by the National Center for Biotechnology Information (NCBI). Blast analysis revealed strong homology to known PAL genes in the database. Compared with the peptide sequences, a 43 nucleotide long intron was identified at position +78.

RACE (Rapid Amplification of cDNA Ends) Cloning of TAL cDNA

Based on the consensus sequence, SEQ ID NO:9, a set of primers was designed for 5' and 3' RACE amplification (Ohara, et al. *PNAS USA* 86:5673 (1989)). These primers are listed in Table 5.

TABLE 5

Primers used to amplify TAL cDNA

| Name | Sequence | Position From AUG | SEQ ID NO: |
|---|---|---|---|
| 5'GSP1a | GGAGGGGCACGCAGGGGACG | 654 | 10 |
| 5'GSP1b | GGAGGGGCACGCAGGGGACGAG | 654 | 11 |
| 5'GSP2 | CGGCAAACGACTGGAGGAC | 634 | 12 |
| 5'GSP3 | TAGGTGGCGTCGGTGGGGAGGAAG | 512 | 13 |
| 5'GSP4 | GGTGGGGAGGAAGCCGCAGAG | 501 | 14 |
| 3'GSP1 | ATGGCCGTCCGCGTCAACAGC | 433 | 15 |
| 3'GSP2 | ATCTCGGCCTCGGGCGACCTCTC | 553 | 16 |
| 3'GSP3 | ACCCCGACGTCAAGGCGTTCG | 611 | 17 |
| 3'GSP4 | GCGATCGCCAAGTACGGCCTCAAGAC | 674 | 18 |
| 3'GSP5 | CCTCCAAGGAGGGCCTCGGCCTCGT | 710 | 19 |
| 3'GSP6 | CTCGCCATCATGAGCCAGACCAACACTG | 793 | 20 |
| AAP | GGCCACGCGTCGACTAGTACGGGGGGGGGG | ---[a] | 21 |
| UAP | CUACUACUACUAGGCCACGCGTCGACTAGTAC | ---[a] | 22 |

[a]These are commercial primers.

5' RACE Cloning of the TAL cDNA

The Poly A(+) RNA of *T. cutaneum* was used for 5'-RACE cloning of tal. A 5'-end RACE kit from Life Technologies was used, following the manufacturer's protocol. The 5'GSP primers listed in Table 5 (SEQ ID NOs:10–14) were used for first strand cDNA synthesis. After purification, a homopolymer tail (poly dC) was added to the end of the cDNA using terminal deoxynucleotide transferase. The tailed cDNA was then amplified by PCR using Qiagen HotStarTaq master mix. The 5' end primer used was AAP (SEQ ID NO:21), and the 3' end primers were 5'GSP1a, 1b, 2, 3, and 4 (SEQ ID NOs:10–14). The PCR conditions used were: 15 min at 94° C., followed by 30 cycles of 30 s at 94° C., 3 min from 80° C. to 55° C. linearly, 1 min at 55° C. and 2 min at 72° C. The PCR products were used as templates for a second round of amplification as shown in Table 6.

TABLE 6

PCR Reactions for Amplifying the 5'-end of tal

| PCR No. | Template | Forward Primer | Reverse Primer |
|---|---|---|---|
| 10 | cDNA w/5'GSP2 | AAP (SEQ ID NO:21) | 5'GSP2 (SEQ ID NO:12) |
| 50 | PCR#10 | UAP (SEQ ID NO:22) | 5'GPS3 (SEQ ID NO:13) |
| 54 | cDNA w/5'GSP1b | AAP (SEQ ID NO:21) | 5'GSP2 (SEQ ID NO:12) |
| 55 | cDNA w/5'GSP1b | AAP (SEQ ID NO:21) | 5'GSP3 (SEQ ID NO:13) |
| 56 | cDNA w/5'GSP2 | AAP (SEQ ID NO:21) | 5'GSP3 (SEQ ID NO:13) |
| 59 | PCR#50 | UAP (SEQ ID NO:22) | 5'GSP4 (SEQ ID NO:14) |
| 60 | PCR#54 | UAP (SEQ ID NO:22) | 5'GSP3 (SEQ ID NO:13) |
| 61 | PCR#54 | UAP (SEQ ID NO:22) | 5'GSP4 (SEQ ID NO:14) |
| 62 | PCR#54 | UAP (SEQ ID NO:22) | 5'GSP4 (SEQ ID NO:14) |
| 63 | PCR#56 | UAP (SEQ ID NO:22) | 5'GSP4 (SEQ ID NO:14) |

The products of PCR nos. 59, 60, 61 and 62 were directly cloned into pCR2.1 by TOPO-TA cloning and transformed into Top10 Chemically Competent E. coli cells. Plasmid DNA from positive clones were isolated and sequenced. The consensus sequence developed is given as SEQ ID NO:23. Compared with the earlier consensus sequence, SEQ ID NO:9, an additional 295 nucleotides upstream of the start codon was included. The intron was still present, suggesting that the mRNA sample used to make the cDNA template may have contained pre-sliced mRNA or a genomic DNA contamination.

3' RACE Cloning of the TAL cDNA

The total RNA was isolated from 100 mL of a culture of T. cutaneum grown to an OD of about 1.2 in Dagley's medium supplemented with tyrosine using an RNeasy kit (Qiagen), following the manufacturer's protocol. The yield was 90 µg of total RNA. Poly A(+) RNAs were purified from the total RNA sample using the Qiagen Oligotex kit, as described above.

The purified polyA(+) RNA sample was used as template for reverse transcription, using the 3' RACE kit and primer AP from Life Technologies (Rockville, Md.). The resulting single stranded cDNA was directly used as template for PCR amplification, using the Advantage G-C cDNA kit from CLONTECH Laboratories (Palo Alto, Calif.). The 5' primers used were 3'GSP1–6 (SEQ ID NOs:15–20) and the 3' primer was AUAP from the RACE kit. Two primer sets 3'GSP4/AUAP and 3'GSP6/AUAP yielded PCR products of the predicted size (1.3 to 1.5 KB). These two PCR products were then cloned into pCR2.1-TOPO (Invitrogen) and sequenced. The two clones overlapped partially with each other and with the consensus sequence, SEQ ID NO:23, indicating that they contained part of the TAL gene. A poly A tail was also present, showing that the end of the coding region was included. These two nucleotide sequences were combined with the consensus sequence SEQ ID NO:23 to produce the complete nucleotide sequence for the TAL gene. The resulting nucleotide sequence for tal and the predicted amino acid sequence based on this nucleotide sequence are given as SEQ ID NO:24 and SEQ ID NO:25, respectively.

The nucleotide sequence obtained for tal (SEQ ID NO:24) was analyzed for similarity to all publicly available DNA sequences by conducting a BLAST (Basic Local Alignment Search Tool; Altschul, S. F., et al., (1993) J. Mol. Biol. 215:403–410; see also www.ncbi.nlm.nih.gov/BLAST/) search for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases) using the BLASTN algorithm provided by the National Center for Biotechnology Information (NCBI). The DNA sequences were translated in all reading frames and compared for similarity to all publicly available protein sequences contained in the "nr" database using the BLASTX BLOSUM62 algorithm with a gap exisitense cost of 11 per residue gap cost of 2, filtered, gap alignment (Gish, W. and States, D. J. Nature Genetics 3:266–272 (1993)) provided by the NCBI.

The results of the BLAST comparison are given in Table 7, which displays data based on the BLASTXnr algorithm with values reported in Expect values. The Expect value estimates the statistical significance of the match, specifying the number of matches, with a given score, that are expected in a search of a database of this size absolutely by chance. The results show that the nucleotide sequence obtained for tal has a high degree of homology to known PAL genes from a variety of organisms. A comparison of the TAL protein sequence (SEQ ID NO:25) with the protein sequence of the TAL from Rhodobacter capsulatus (Kyndt et al., FEBS Letters 512:240–244 (2002)) gave a 28% identity.

TABLE 7

BLAST Comparison of TAL Gene (SEQ ID NO:24)

| GENE | SIMILARITY IDENTIFIED | % IDENTITY[A] | % SIMILARITY[B] | E-VALUE[C] | CITATION |
|---|---|---|---|---|---|
| Tal [*T. cutaneum*] | PAL [*R. toruloides*] | 48 | 62 | e-161 | Anson, J. G. et al, Gene 58, 189–199 (1987) |
| | PAL [*R. toruloides*] | 48 | 62 | e-161 | Rasmussen, O. F. et al, DNA Seq. 1, 207–211 (1991) |
| | PAL [*R. rubra*] | 47 | 62 | e-160 | Filpula, D. et al, Nucleic Acids Res. 16, 11381 (1988) |
| | PAL [*R. toruloides*] | 47 | 61 | e-157 | Anson, J. G. et al Gene 58, 189–199 (1987) |
| | PAL [*Amanita muscaria*] | 39 | 56 | e-123 | Nehls, U. et at J. Bacteriol. 181, 1931–1933 (1999) |
| | PAL [*Ustilago maydis*] | 39 | 56 | e-121 | Kim, S. H. et al unpublished |

[A]% Identity is defined as percentage of amino acids that are identical between the two proteins.
[B]% Similarity is defined as percentage of amino acids that are identical or conserved between the two proteins.
[C]Expect value. The Expect value estimates the statistical significance of the match, specifying the number of matches, with a given score, that are expected in a search of s database of this size absolutely by chance. % Identity, % Similarity, and E-values are all reported according to FASTA analysis with Smith-Waterman computation.

Example 6

Expression of the TAL Gene in the Yeast *Saccharomyces cerevisiae*

The purpose of this Example was to express the TAL gene in the yeast *Saccharomyces cerevisiae*. Expression was confirmed by measuring the levels of PHCA and CA produced by the yeast transformants.

Expression of tal in the Yeast *Saccharomyces cerevisiae*

A 2070 bp DNA fragment containing the coding region of tal was amplified from genomic DNA in two steps to remove the intron. This fragment was then cloned into the vector pYES2.0 (Invitrogen, Carlsbad, Calif.) under the control of the yeast GAL1 promoter.

The primers SEQ ID NOs:26 and 27 were used to amplify a 97 bp fragment using *T. cutaneum* genomic DNA as template, removing a 43 bp intron between nucleotides 78 and 121. A second 2033 bp fragment was amplified from *T. cutaneum* genomic DNA using primers SEQ ID Nos:28 and 29. In both cases, the PCR reaction mixture contained 1 μL of genomic DNA, 1 μL each of the two primers (at 20 μM), 10 μL of 10×PCR buffer, 10 μL of 5 M G-C melt, 8 μL of 2.5 mM dNTP, 18 μL of $H_2O$, and 1 μL of Advantage G-C polymerase mix (CLONTECH Laboratories). The reaction mixture was heated to 94° C. for 2.5 min, then cycled as follows: 30 cycles of 30 s at 94° C., 30 s at 55° C., and 2 min at 72° C., followed by 7 min at 72° C.

The PCR products were purified with Qiaquick PCR purification kit (Qiagen Inc., Valencia, Calif.), diluted 1:10 with $H_2O$ and mixed in equal volume. One microliter of the mixed PCR products was used as template for a second round of amplification with the primers SEQ ID NOs:30 and 31. PCR conditions were exactly the same as in the first round. The reaction mixture contained the same ingredients except for the different primers and template. The resulting 2070 bp DNA fragment was purified with Qiaquick PCR purification kit, digested with EcoRI and XbaI and cloned into the EcoRI-XbaI sites of pYES2.0.

Fifteen colonies from the transformation plate were used to inoculate separate 2 mL portions of LB liquid culture medium consisting of 1% Bacto-Tryptone, 0.5% Bacto-Yeast Extract, 0.5% NaCl, 1 mM NaOH and 100 μg/mL ampicilin. These cultures were incubated overnight. Plasmid DNA was purified from these cultures using a Qiagen Miniprep kit, following the manufacturer's protocol. Restriction digestion with XhoI showed that 12 out of the 15 plasmids contained the tal insert.

The 12 clones were pooled together and used to transform the yeast *Saccharomyces cerevisiae* W1362-17A. Yeast cells were grown in YPD medium (1% Bacto-Yeast Extract, 2% Bacto-Peptone, and 2% dextrose) overnight at 30° C., diluted to an OD of 0.2 at 600 nm and grown for another 5 h. Fifty milliliters of the culture was centrifuged, washed 3 times with 1 mL 0.1 M lithium acetate and resuspended in 50 μL of 0.1 M lithium acetate. Forty microliters of this suspension was mixed with 10 μL of 10 mg/mL salmon sperm DNA, 1 μL of the pooled plasmid DNA and 300 μL of 40% PEG 3350. The mixture was incubated at 30° C. for 30 min, followed by the addition of 40 μL of dimethyl sulfonate and incubated at 42° C. for 20 min. The mixture was centrifuged and the cells were resuspended in $H_2O$ and spread on a SD medium plate (0.67% yeast nitrogen base, 2% dextrose, 2% Bacto-Agar).

Eight individual yeast transformants were selected and grown in SR liquid medium (0.67% yeast nitrogen base, and 2% raffinose) overnight. The cultures were diluted to an OD of 0.5 in SG medium (0.67% yeast nitrogen base, and 2% galactose), allowed to grown for 4 h, and then supplemented with 10× amino acids (*Guide to Yeast Genetics and Molecular Biology*, Meth. Enzymol. Eds. C. Guthrie and G. R. Fink. Vol. 194, p. 15) without uracil. After another 4 h of growth, the cultures were centrifuged and the supernatant was tested for the presence of PHCA and CA using HPLC (High Performance Liquid Chromatography), as described below.

HPLC Determination of PHCA and CA

The culture medium was centrifuged and 20–1000 μL of the supernatant was acidified with phosphoric acid, filtered through a 0.45 micron filter and analyzed by HPLC to determine the concentration of PHCA and CA in the growth medium.

A Hewlett Packard 1090L HPLC system with an auto sampler and a diode array UV/vis detector was used with a reverse-phase Zorbax SB-C8 column (4.6 mm×250 mm), supplied by MAC-MOD Analytical Inc. (Chadds Ford, Pa.). A flow rate of 1.0 mL per min was used with Solvent A (methanol) and Solvent B (0.2% trifluoroacetic acid (TFA) in water) with the solvent gradient given in Table 8. The column temperature was maintained at 40° C. The UV detector was set to monitor the eluant at 250, 230, 270, 290 and 310 nm wavelengths.

TABLE 8

Solvent Gradient for HPLC Determination of PHCA and CA

| Time (min) | Solvent A Methanol | Solvent B 0.2% TFA |
|---|---|---|
| 0.0 | 10% | 90% |
| 0.1 | 10% | 90% |
| 9.0 | 35% | 65% |
| 9.1 | 50% | 50% |
| 14.0 | 50% | 50% |
| 18.0 | 100% | 0% |
| 21.0 | 100% | 0% |

At these conditions, PHCA and CA had retention times of 14.0 and 17.6 min, respectively.

As shown in Table 9, all 8 cultures grown in the presence of amino acids, contained some levels of PHCA but no detectable CA, demonstrating successful expression of the TAL gene.

TABLE 9

PHCA and CA Levels in Yeast Cultures.

| Clones | Growth Media | PHCA Concentration |
|---|---|---|
| 1 | SG | none detected |
| 2 | SG | none detected |
| 3 | SG | none detected |
| 4 | SG | none detected |
| 5 | SG | none detected |
| 6 | SG | none detected |
| 7 | SG | none detected |
| 8 | SG | none detected |
| 1 | SG plus amino acids | 2.8 µM |
| 2 | SG plus amino acids | <1.5 µM |
| 3 | SG plus amino acids | <1.5 µM |
| 4 | SG plus amino acids | 2.0 µM |
| 5 | SG plus amino acids | 2.0 µM |
| 6 | SG plus amino acids | 1.5 µM |
| 7 | SG plus amino acids | 3.3 µM |
| 8 | SG plus amino acids | 2.2 µM |

Example 7

Expression of the TAL Gene in *E. coli*

The purpose of this Example was to express the TAL gene in the bacterium *E. coli*.

The coding region of the *T. cutaneum* TAL gene without the intron (see Example 6) was amplified by PCR using the following primers: SEQ ID NO:32 (forward) and SEQ ID NO:33 (reverse). The PCR reaction mixture contained 1 µL of template DNA (tal in pTricHis-ToPo), 1 µL each of the two primers (at 20 µM), 10 µL of 10×PCR buffer, 10 µL of 5 M G-C melt, 8 µL of 2.5 mM dNTP, 18 µL of H$_2$O, and 1 µL of Advantage G-C polymerase mix (CLONTECH Laboratories). The reaction mixture was heated to 94° C. for 2.5 min, then cycled as follows: 30 cycles of 30 s at 94° C., 30 s at 55° C., and 2 min at 72° C., followed by 7 min at 72° C.

The amplified PCR product was purified using the Qiagen PCR purification kit (Qiagen Inc.) and eluted with 50 µL of buffer EB supplied with the kit. Twenty five microliters of the purified PCR product was mixed with 25 µL of water, 6 µL of New England BioLab restriction Buffer 2 (New England BioLabs), and 2 µL each of NdeI and HindIII (New England BioLabs). The mixture was incubated at 37° C. for 4 h.

A plasmid designated as pBX2 was prepared as follows. The plasmid pRSET-B, obtained from Invitrogen, was digested with NcoI (New England BioLabs), filled with DNA Polymerase Large (Klenow) Fragment (New England BioLabs) and religated. The resulting plasmid, designated as "plasmid A", was digested with XbaI and BamHI. A 109 base pair fragment was excised from the plasmid pET14-b (Novagen) using XbaI and BamHI, and was ligated into plasmid A, resulting in "plasmid B". Plasmid B was then digested with NdeI and BamHI. A plant genomic DNA fragment from *Oryza sativa*, Nipponbare strain, clone OJ1125B03, from chromosome 3 (McCombie et al, GenBank AC134885), having the sequence designated as SEQ ID NO:34, was digested with NdeI and BamHI, and ligated with the digested plasmid B to give plamid pBX2.

Approximately 4 µg of plasmid pBX2 was digested with NdeI and HindIII, as described above, to remove the DNA fragment designated as SEQ ID NO:34. This allowed easy separation and purification of the 2.9 kDa vector by gel electrophoresis, followed by extraction using the Qiagen Gel Extraction kit according to the manufacturer's protocol. The digested PCR product containing tal, prepared as described above, was purified using the Qiagen PCR Purification kit. Purified pBX2 and the PCR product were ligated using T4 DNA ligase (Promega, Madison, Wis.) following the manufacturer's protocol. The ligation mixtures were used to transform TOPO10 Chemically Competent *E. coli* cells (Invitrogen) following the manufacturer's protocol.

Fifteen colonies from the transformation plate were used to inoculate separate 2 mL portions of LB liquid culture medium consisting of 1% Bacto-Tryptone, 0.5% Bacto-Yeast Extract, 0.5% NaCl, 1 mM NaOH and 100 µg/mL ampicilin. These cultures were incubated overnight. Plasmid DNA was purified from these cultures using a Qiagen Miniprep kit, following the manufacturer's protocol. Restriction digestion of the plasmid DNA with the enzyme NcoI (New England BioLabs) showed that 4 out of the 15 plasmids contained the tal insert. This plasmid was named pTAL-BX2.

One of the correct clones was used to transform *E. coli* BL21-codon plus-DE3-RP competent cells (Stratagene, La Jolla, Calif.). As a control, pBX2 plasmid was also used to transform the same strain separately. One colony from each transformation was picked to inoculate 2 mL of LB liquid culture medium consisting of 1% Bacto-Tryptone, 0.5% Bacto-Yeast Extract, 0.5% NaCl, 1 mM NaOH and 100 µg/mL ampicilin. These cultures were allowed to grow overnight at 37° C., and then were diluted into 15 mL of the same medium and grown to an OD of about 0.4 at 600 nm measured at room temperature. One milliliter of each culture was taken and centrigfuged at 14,000 rpm in a microcentrifuge (Eppendorf Microfuge, Brinkmann Instruments, Westbury, N.Y.) for 2 min. Cell pellets were dissolved in 40 µL of SDS sample buffer (0.1 M Tris-HCl, pH 6.8, 4% SDS, 20% glycerol, 0.002% bromophenol blue). β-mercaptoethanol (20 µL) was added to 1 mL of the buffer before use. IPTG was added to a final concentration of 0.7 mM to the remaining cultures. The cultures were then grown for an additional 18 h at room temperature. One milliliter of each of these overnight cultures was taken and centrifuged at 14,000 rpm in a microcentrifuge (Eppendorf) for 2 min. The resulting cell pellets were each resuspended in 120 µL of SDS sample buffer and were designated as the "whole cell" samples.

The overnight cultures (10 mL of each) were centrifuged at 5,000 rpm at 4° C. in a Sorvall RC5B centrifuge (Kendro Laboratory Products, Newtown, Conn.) using a SS34 rotor. The cell pellets were washed once with 0.5 mL of 0.1 M phosphate buffer, pH 7.5, containing the Complete Mini Protease Inhibitor Cocktail Tablet (1 tablet/10 mL buffer), obtained from Roche Molecular Biochemicals (Indianapolis, Ind.). After washing, the cell pellets were each resuspended in 1 mL of the above buffer and sonicated 5 times for 15 s on ice using a Fisher Model 300 Sonic Dismembrantor (Fisher Scientific Co., Pittsburgh, Pa.), fitted with a microtip, at a power setting at 60. The suspensions were centrifuged at 15,300 rpm for 30 min at 4° C. in a microcentrifuge (Beckman Coulter Inc., Fullerton, Calif.). Five microliters of each supernatant was mixed with 5 µL of SDS sample buffer. These samples were designated as the "soluble fractions".

Each pellet was resuspended in 500 µL of 0.1 M phosphate buffer plus protease inhibitors, and mixed with 500 µL of SDS sample buffer. These samples were designated as the "insoluble fractions". Each of the whole cell, soluble and insoluble fractions (10 µL) were loaded onto a NuPAGE® Gel System 4–12% bis-tris SDS gel (Invitrogen) and electrophoresis was performed according to manufacturer's protocol.

Figure 3:
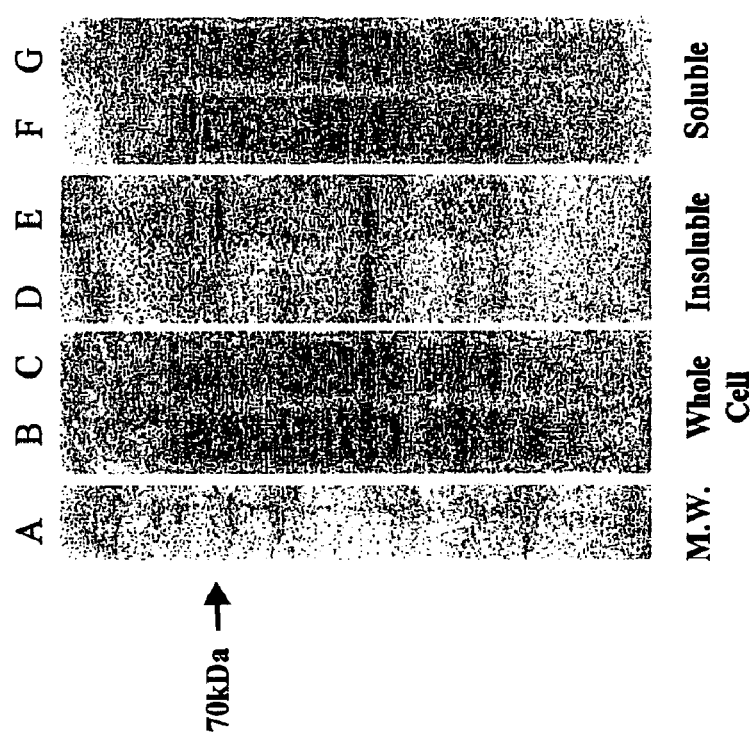
FIG. 3 is a gel image of the polyacrylamide gel electrophoresis gel of *E. coli* cell extracts from cells transformed with pTAL-BX2.

The resulting gel image is shown in FIG. 3. On the gel image, lane A is the molecular weight marker Mark 12 (Invitrogen), lanes B, D, and F are control samples containing the pBX2 plasmid from whole cells, the insoluble fraction and the soluble fraction, respectively, prepared from E. coli cells carrying the pBX2 plasmid as described above. Lanes C, E, and G are samples of whole cells, the insoluble fraction and the soluble fraction, respectively, prepared from E. coli cells that contain the pTAL-BX2 plasmid as described above. As shown in the Figure, lane E has a protein band of the expected molecular weight for TAL, approximately 70 kDa, which is absent in the control (Lane D), demonstrating the successful expression of TAL in E. coli. However, the expressed protein had very low enzyme activity, indicating that further optimization of the expression system is required. The TAL protein is not present in the soluble fraction (lane G), indicating that it is not soluble when expressed under the conditions described above.

What is claimed is:

1. An isolated nucleic acid molecule encoding a tyrosine ammonia lyase enzyme, selected from the group consisting of:
   a) an isolated nucleic acid molecule encoding the amino acid sequence as set forth in SEQ ID NO:25;
   b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS at 65° C.; or an isolated nucleic acid molecule that is complementary to (a) or (b).

2. An isolated nucleic acid molecule as set forth in SEQ ID NO:24.

3. A transformed host cell comprising the isolated nucleic acid molecule of claim 1 or 2.

4. The transformed host cell of claim 3 wherein the host cell is a cell selected from the group consisting of bacteria, yeast, filamentous fungi, algae, and green plants.

5. The transformed host cell of claim 4 wherein the host cell is a microorganism selected from the group consisting of *Escherichia, Salmonella, Bacillus, Acinetobacter, Streptomyces, Methylobacter, Rhodococcus, Pseudomonas, Rhodobacter, Synechocystis, Aspergillus, Arthrobotrys, Saccharomyces, Zygosaccharomyces, Kluyveromyces, Candida, Hansenula, Debaryomyces, Pichia, Mucor, Torulopsis, Spirulina, Haemotacoccus*, and *Dunalliela*.

6. The transformed host cell of claim 3 wherein the host cell is a plant cell selected from the group consisting soybean, rapeseed, pepper, sunflower, cotton, corn, tobacco Alfalfa, wheat, barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grass.

7. A method of obtaining a nucleic acid molecule encoding a tyrosine ammonia lyase enzyme comprising:
   a) probing a genomic library with the nucleic acid molecule of any one of claims 1 or 2;
   b) identifying a DNA clone that hybridizes with the nucleic acid molecule of any one of claims 1 or 2 under the following hybridization conditions: 0.1×SSC, 0.1% SDS, at 65° C. and washed with 2×SSC, 0.1% SDS followed by 0.1×SSC, 0.1% SDS at 65° C.; and
   c) sequencing the genomic fragment that comprises the clone identified in step (b),
   wherein the sequenced genomic fragment encodes a tyrosine ammonia lyase enzyme.

8. A method for the production of para-hydroxycinnamic acid para-hydroxycinnamic acid (PHCA) comprising:
   (a) contacting a recombinant host cell with a fermentable carbon substrate, said recombinant cell comprising the isolated nucleic acid molecule of claim 1 or 2;
   (b) growing said recombinant cell for a time sufficient to produce PHCA; and
   (c) optionally recovering said PHCA.

9. A method according to claim 8 wherein said fermentable carbon substrate is selected from the group consisting of monosaccharides, oligosaccharides, polysaccharides, carbon dioxide, methanol, formaldehyde, formate, and carbon-containing amines.

10. A method according to claim 9 wherein said fermentable carbon substrate is glucose.

11. A method according to claim 8 wherein said recombinant host cell is a cell selected from the group consisting of bacteria, yeasts, filamentous fungi, algae and plant cells.

12. A method according to claim 11 wherein said recombinant host cell is a microorganism selected from the group consisting of *Escherichia, Salmonella, Bacillus, Acinetobacter, Streptomyces, Methylobacter, Rhodococcus, Pseudomonas, Rhodobacter, Synechocystis, Aspergillus, Arthrobotrys, Saccharomyces, Zygosaccharomyces, Kluyveromyces, Candida, Hansenula, Debaryomyces, Pichia, Mucor, Torulopsis, Spirulina, Haemotacoccus*, and *Dunalliela*.

13. A method according to claim 8 wherein said recombinant host cell is a plant cell selected from the group consisting of soybean, rapeseed, sunflower, cotton, corn, tobacco, alfalfa, wheat, barley, oats, sorghum, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

14. The method according to claim 8 wherein said isolated nucleic acid molecule encoding a tyrosine ammonia lyase activity encodes the peptide set forth in SEQ ID NO:25.

15. The method according to claim 8 wherein the isolated nucleic acid molecule encoding a tyrosine ammonia lyase activity is isolated from *Trichosporon cutaneum*.

* * * * *